(12) United States Patent
Worden et al.

(10) Patent No.: US 10,246,786 B2
(45) Date of Patent: *Apr. 2, 2019

(54) RENEWABLE BIOELECTRONIC INTERFACE FOR ELECTROBIOCATALYTIC REACTOR

(71) Applicant: Board of Trustees of Michigan State University, East Lansing, MI (US)

(72) Inventors: Robert Mark Worden, Holt, MI (US); Brian L. Hassler, Lake Orion, MI (US); Lawrence T. Drzal, Okemos, MI (US); Ilsoon Lee, Okemos, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 213 days.

This patent is subject to a terminal disclaimer.

(21) Appl. No.: 15/177,668

(22) Filed: Jun. 9, 2016

(65) Prior Publication Data

US 2016/0326658 A1 Nov. 10, 2016

Related U.S. Application Data

(63) Continuation of application No. 12/766,169, filed on Apr. 23, 2010, now Pat. No. 9,406,959.

(Continued)

(51) Int. Cl.
*C25B 11/04* (2006.01)
*C12M 1/34* (2006.01)
(Continued)

(52) U.S. Cl.
CPC .......... *C25B 11/0489* (2013.01); *C12Q 1/005* (2013.01); *C25B 11/0405* (2013.01);
(Continued)

(58) Field of Classification Search
CPC . C12Q 1/005; C25B 11/0489; C25B 11/0415; C25B 11/0405; G01N 27/3272; H01M 4/9008; H01M 8/16; Y02E 60/527
(Continued)

(56) References Cited

U.S. PATENT DOCUMENTS 4,430,176 A 2/1984 Davison
5,520,786 A 5/1996 Bloczynski et al.
(Continued)

FOREIGN PATENT DOCUMENTS

WO 2007078315 A2 7/2007

OTHER PUBLICATIONS

Weibel, et al., The Glucose Oxidase Mechanism, The Journal of Biological Chemistry, Dec. 2, 1970, pp. 2734-2744, vol. 246, No. 9.
(Continued)

*Primary Examiner* — Michael L Hobbs
(74) *Attorney, Agent, or Firm* — Clark IP Law, PLC

(57) ABSTRACT

An inexpensive, easily renewable bioelectronic device useful for bioreactors, biosensors, and biofuel cells includes an electrically conductive carbon electrode and a bioelectronic interface bonded to a surface of the electrically conductive carbon electrode, wherein the bioelectronic interface includes catalytically active material that is electrostatically bound directly or indirectly to the electrically conductive carbon electrode to facilitate easy removal upon a change in pH, thereby allowing easy regeneration of the bioelectronic interface.

30 Claims, 17 Drawing Sheets

Related U.S. Application Data

(60) Provisional application No. 61/172,337, filed on Apr. 24, 2009.

(51) Int. Cl.
  *H01M 8/16* (2006.01)
  *C12Q 1/00* (2006.01)
  *G01N 27/327* (2006.01)
  *H01M 4/90* (2006.01)

(52) U.S. Cl.
  CPC ...... *C25B 11/0415* (2013.01); *G01N 27/3272* (2013.01); *H01M 4/9008* (2013.01); *H01M 8/16* (2013.01); *Y02E 60/527* (2013.01)

(58) Field of Classification Search
  USPC ....... 204/400, 252, 290.11, 290.07; 977/742, 977/734; 427/458; 435/287.9
  See application file for complete search history.

(56) References Cited

U.S. PATENT DOCUMENTS

| | | | |
|---|---|---|---|
| 6,475,750 | B1 | 11/2002 | Han et al. |
| 6,720,164 | B1 | 4/2004 | Shinozuka et al. |
| 7,291,256 | B2 | 11/2007 | Teodorczyk et al. |
| 7,749,772 | B1 | 7/2010 | Wang |
| 8,435,773 | B2* | 5/2013 | Worden ........... B82Y 30/00 204/403.14 |
| 8,623,196 | B2 | 1/2014 | Kohli et al. |
| 9,406,959 | B2* | 8/2016 | Worden ........... H01M 8/16 |
| 2001/0017269 | A1 | 8/2001 | Heller et al. |
| 2004/0050717 | A1 | 3/2004 | Teodorczyk et al. |
| 2004/0101741 | A1 | 5/2004 | Minteer et al. |
| 2008/0160384 | A1 | 7/2008 | Iqbal et al. |
| 2009/0000957 | A1* | 1/2009 | Dubin ........... B01J 19/0046 205/701 |
| 2009/0130698 | A1 | 5/2009 | Worden et al. |
| 2010/0023101 | A1 | 1/2010 | Wallace et al. |
| 2010/0314248 | A1 | 12/2010 | Worden et al. |

OTHER PUBLICATIONS

Willner, et al., Electrical Wiring of Glucose Oxidase by Reconstitution of FAD-Modified Monolayers Assembled onto Au-Electrodes, J. Am. Chem. Soc., 1996, pp. 10321-10322, vol. 118.
Winder, A Stopped Spectrophotometric Assay for the Dopa Oxidase Activity of Tyrosinase, J. Biochem. Biophys. Methods, 1994, pp. 173-183, vol. 28, Elsevier B.V.
Wong, et al., Lateral Flow Immunoassay, 2009, 223 pages.
Zayats, et al., Electrical Contacting of Flavoenzymes and NAD (P)+-Dependent Enzymes by Reconstitution and Affinity Interactions on Phenylboronic Acid Monolayers Associated with Au-Electrodes, JACS, 2002, 12 pages, vol. 124, American Chemical Society.
Zhao, et al., Scanning Electrochemical Microscopy of Quinoprotein Glucose Dehydrogen, Anal. Chem., 2004, pp. 3145-3154, vol. 76, No. 11, American Chemical Society.
Carralero, et al., Amperometric IgG Immunosensor Using a Tyrosinase-Colloidal Gold-Graphite-Teflon Biosensor as a Transducer, ResearchGate, Feb. 2008, 17 pages, pp. 244-259, vol. 41, Taylor & Francis Group, LLC.
G-Biosciences, Double-Do Protein Cross-Linkers, Handbook & Selection Guide, 2017, 16 pages, http://wolfson.huji.ac.il/purification/PDF/ProteinInteractions/GBIOSC_ProtCrossLinkersHandbook.pdf.
Nucleic Acid Lateral Flow, Feb. 19, 2017, 2 pages, http://www.dcndx.com/application-detail/nucleic-acid-lateral-flow.
Thermo Scientific Pierce Assay Development Technical Handbook, Version 2, 76 pages.
Advisory Action received for U.S. Appl. No. 11/914,340, dated Jul. 5, 2012, 3 pages.
Final Office Action received for U.S. Appl. No. 11/914,340, dated Mar. 12, 2012, 7 pages.
Issue Notification received for U.S. Appl. No. 11/914,340, dated Apr. 17, 2013, 1 page.
Non Final Office Action received for U.S. Appl. No. 11/914,340, dated Nov. 30, 2011, 7 pages.
Notice of Allowance received for U.S. Appl. No. 11/914,340, dated Feb. 11, 2013, 9 pages.
Request for Continued Examination filed for U.S. Appl. No. 11/914,340, dated Jul. 12, 2012, 1 page.
Notice of Allowance received for U.S. Appl. No. 12/766,169, dated Mar. 1, 2016, 10 pages.
Advisory Action received for U.S. Appl. No. 12/766,169, dated Dec. 14, 2015, 4 pages.
Final Office Action received for U.S. Appl. No. 12/766,169, dated Sep. 29, 2015, 22 pages.
Non Final Office Action received for U.S. Appl. No. 12/766,169, dated May 28, 2015, 18 pages.
Non Final Office Action received for U.S. Appl. No. 12/766,169, dated Jan. 22, 2013, 15 pages.
Final Office Action received for U.S. Appl. No. 15/383,320, dated Sep. 17, 2018, 17 pages.
Non Final Office Action received for U.S. Appl. No. 15/383,320, dated Jun. 5, 2018, 13 pages.
Bahadir, et al., Applications of commercial biosensors in clinical, food, environmental, and biothreat/biowarfare analyses, Analytical Biochemistry, Science Direct, Mar. 26, 2015, 14 pages, Elseveir Inc.
Berg, et al., Tailored Micropatterns through Weak Polyelectrolyte Stamping, Langmuir, 2003, pp. 2231-2237, vol. 19, American Chemical Society.
Blaedel, et al., Study of the Electrochemical Oxidation of Reduced Nicotinamide Adenine Dinucleotide, Analytical Chemistry, Jul. 1975, pp. 1337-1343, vol. 47, No. 8.
Bourdillon, et al., A Fully Active Monolayer Enzyme Electrode Derivatized by Antigen-Antibody Attachment, J. Am. Chem. Soc., 1993, pp. 12264-12269, vol. 115, American Chemical Society.
Bradshaw, et al., A Pseudomonas sp. Alcohol Dehydrogenase with Broad Substrate Specificity and Unusual Stereospecificity for Organic Synthesis, J. Org. Chem., 1992, 7 pages, vol. 57, No. 5, American Chemical Society.
Bradshaw, et al., Lactobacillus kefir Alcohol Dehydrogenase: A Useful Catalyst for Synthesis, J. Org. Chem., 1992, 5 pages, vol. 57, No. 5, American Chemical Society.
Burdette, et al., Cloning and Expression of the Gene Encoding the Thermoanaerobacter Ethanolicus 39e Secondary-Alcohol Dehydrogenase and Biochemical Characterization of the Enzyme, Biochem. J., 1996, pp. 115-122, vol. 316.
CHeng, et al., Ultrathin Polypeptide Multilayer Films for the Fabrication of Model Liquid/Liquid Electrochemical Interfaces, J. Phys. Chem, 1999, pp. 8726-8731, vol. 103, American Chemical Society.
Clark, et al., The Role of Secondary Interactions in Selective Electrostatic Multilayer Deposition, Langmuir, 2000, pp. 10206-10214, vol. 16, American Chemical Society.
Degani, et al., Direct Electrical Communication Between Chemically Modified Enzymes and Metal Electrodes. I. Electron Transfer from Glucose Oxidase to Metal Electrodes via Electron Relays, Bound Covalently to the Enzyme, the Journal of Physical Chemistry, Mar. 12, 1987, 5 pages, vol. 91, No. 6, American Chemical Society.
Escamilla-Gomez, et al., Immunosensor for the Determination of *Staphylococcus aureus* Using a Tyrosinase-Mercaptopropionic Acid Modified Electrode as an Amperometric Transducer, Anal. Bioanal. Chem., 2008, pp. 837-845, vol. 391, Springer.
Fjeld, et al., Differential Binding of NAD+ and NADH Allows the Transcriptional Corepressor Carboxyl-Terminal Binding Protein to Serve as a Metabolic Sensor, PNAS, Aug. 5, 2003, pp. 9202-9207, vol. 100, No. 16.
Forster, et al., Kinetic Separation of Faradaic Currents: Binary Monolayers as Model Systems, Anal. Chem., 1995, pp. 1232-1239, vol. 67, American Chemical Society.

(56) References Cited

OTHER PUBLICATIONS

Forster, Electron Transfer Dynamics and Surface Coverages of Binary Anthraquinone Monolayers on Mercury Microelectrodes, Langmuir, 1995, pp. 2247-2255, vol. 11, American Chemical Society.

Friedrich, et al., Reticulated vitreous carbon as an electrode material, Journal of Electroanalytical Chemistry, 2004, pp. 203-217, vol. 561, Elsevier B.V.

Hayat, et al., Disposable Screen Printed Electrochemical Biosensors: Tools for Environmental Monitoring, Sensors, 2014, 22 pages, vol. 14.

Heller, Adam, Electrical Wiring of Redox Enzymes, Acc. Chem. Res., 1990, 7 pages, vol. 23, No. 5, American Chemical Society.

James, et al., Novel Saccharide-Photoinduced Electron Transfer Sensors Based on the Interaction of Boronic Acid and Amine, J. Am. Chem. Soc., 1995, pp. 8982-8987, vol. 117, American Chemical Society.

Keinan, et al., Thermostable Enzymes in Organic Synthesis. 2. Asymmetric Reduction of Ketones with Alcohol Dehydrogenase from Thermoanaerobium brockii, J. Am. Chem. Soc., 1986, pp. 162-169, vol. 108, American Chemical Society.

Kohli, et al., Nanostructured Biosensor for Measuring Neuropathy Target Esterase Activity, Anal. Chem., 2007, pp. 5196-5203, vol. 79, American Chemical Society.

Kohli, et al., Theoretical and Experimental Study of Bi-Enzyme Electrodes with Substrate Recycling, Journal of Electroanalytical Chemistry, 2010, pp. 104-110, vol. 641, Elsevier B.V.

Kotanen, et al., Implantable enzyme amperometric biosensors, Biosensors and Bioelectronic, 2012, pp. 14-26, vol. 35, Elsevier B.V.

Kricka, Selected Strategies for Improving Sensitivity and Reliability of Immunoassays, Clin. Chem., 1994, pp. 347-357, vol. 40, No. 3.

Loew et al. Characterization of Self-Assembling of Glucose Dehydrogenase in Mono- and Multilayers on Gold Electrodes, Electroanalysis, 2004, 6 pages, vol. 16, No. 13-14, Wiley-VCH.

O'Farrell, Lateral flow immunoassay systems: evolution from the current state of the art to the next generation of highly sensitive, quantitative rapid assays, pp. 89-107, Chapter 2.4.

Pariente, et al., Electrocatalysis of NADH Oxidation with Electropolymerized Films of 3,4- Dihydroxybenzaldehyde, Anal. Chem., Dec. 1, 1994, pp. 4337-4344, vol. 66, No. 23, American Chemical Society.

International Search Report and Written Opinion received for PCT Patent Application No. PCT/US2006/018083, dated Apr. 17, 2008, 9 pages.

Pogorelova, et al., Analysis of NAD(P)+/NAD(P)H Cofactors by Imprinted Polymer Membranes Associated with on-Sensitive Field-Effect Transistor Devices and Au-Quartz Crystals, Anal. Chem., 2003, pp. 509-517, vol. 75, No. 3, American Chemical Society.

Prodromidis, et al., Enzyme Based Amperometric Biosensors for Food Analysis, Electroanalysis, 2002, 21 pages, vol. 14, No. 4, Wiley-VCH.

Raitman, et al., Electrical Contacting of Glucose Dehydrogenase by the Reconstitution of a Pyrroloquinoline Quinone-Functionalized Polyaniline Film Associated With an Au-Electrode: An in Situ Electrochemical SPR Study, Chem. Commun., 2002, pp. 1936-1937, The Royal Society of Chemistry.

Ramanavicius, et al., Polypyrrole-Entrapped Quinohemoprotein Alcohol Dehydrogenase. Evidence for Direct Electron Transfer via Conducting-Polymer Chains, Analytical Chemistry, 1999, pp. 3581-3586, vol. 71, No. 16.

Schmakel, et al., Nicotinamide Adenine Dinucleotide (Nad+) and Related Compounds. Electrochemical Redox Pattern and Allied Chemical Behavior, Journal of the American Chemical Society, Sep. 3, 1975, 10 pages, vol. 97, No. 18.

Schmidt, et al., Coenzyme Properties of NAD+ Bound to Different Matrices through the Amino Group in the 6-Position, 1976, pp. 295-302, vol. 67.

Schuhmann, et al., Electron Transfer between Glucose Oxidase and Electrodes via Redox Mediators Bound with Flexible Chains to the Enzyme Surface, J. Am. Chem. Soc., 1991, pp. 1394-1397, vol. 113, American Chemical Society.

* cited by examiner

RENEWABLE BIOELECTRONIC INTERFACE FOR ELECTROBIOCATALYTIC REACTOR

CROSS-REFERENCE TO RELATED APPLICATION

This application is a continuation of U.S. application Ser. No. 12/766,169, filed Apr. 23, 2010, entitled ELECTROBIOCATALYTIC REACTORS HAVING REVERSIBLE BIOELECTRONIC INTERFACES AND METHODS AND DEVICES RELATED THERETO, now issued as U.S. Pat. No. 9,406,959, which application claimed the benefit of U.S. Provisional Application Ser. No. 61/172,337, filed May 24, 2009, entitled BIOELECTRONIC INTERFACE DEVICE, each of which is hereby incorporated by reference herein in its entirety.

FIELD OF THE INVENTION

The present invention relates to bioelectronic interfaces that promote electrical communication between a catalytically active material and an electrode to facilitate chemical reactions in an electrobiocatalytic reactor, to produce electricity in a biofuel cell, or to detect an analyte with a biosensor.

BACKGROUND OF THE INVENTION

Bioelectronic interfaces that achieve electrical communication between redox enzymes and an electrode have applications as biosensors (Armstrong et al., 1997, Halbhuber et al., 2003, Zayats et al., 2002), biocatalysts (Park et al., 1999, Park et al., 2003, Park and Zeikus, 1999, Tsujimura et al., 2001), and biofuel cells (Chen et al., 2001, Park and Zeikus, 2003). Development of bioelectronic interfaces is especially challenging for dehydrogenase enzymes, whose activity requires the presence of an electron carrying cofactor [e.g., β-nicotinamide adenine dinucleotide (phosphate) (NAD(P)$^+$)] in the Rossmann fold of the enzyme. The cofactor facilitates the transfer of electrons between the redox center of the enzyme and the electrode. However, direct electrochemical oxidation of NADH requires the use of high overpotentials, which may lead to cofactor degradation (Blaedel and Jenkins, 1975, Schmakel et al., 1975). Cofactor degradation can be circumvented using an electron mediator, such as toluidine blue O (TBO), Nile blue A, or neutral red to shuttle electrons between the electrode and cofactor at moderate potentials (Molina et al., 1999, Pasco et al., 1999).

Several approaches have been used to achieve mediated electron exchange, including the development of linear (Zayats et al., 2002, Hassler et al., 2007) and branched (Hassler et al., 2007, Hassler and Worden, 2006) molecular architectures that simultaneously hold the electrode, mediator, cofactor, and enzyme in close proximity, allow unimpeded access of the cofactor to its binding site on the enzyme, provide efficient, multistep electron transfer, and prevent component loss due to diffusion. However, these fabrication methods involve covalent linkages and make no provision for removal and replacement of labile components, such as the enzyme and cofactor, which have limited lifetimes. Long-term operation requires interface assembly methods that allow periodic removal and replacement of these components.

A method to fabricate renewable bioelectronic interface on gold electrodes (Hassler et al., 2007) has been developed. This method allows facile removal and replacement of the cofactor and enzyme. The approach uses layer-by-layer deposition of polyelectrolytes to reversibly bind the cofactor and enzyme, so that they can be removed by reducing pH and then replaced to regenerate the bioelectronic activity (Hassler et al., 2007).

However, because this method uses a thiol linkage to anchor the interface to the gold electrode, it may not be suitable for other electrode materials. In addition, thiol bonds may have disadvantages for certain applications. Alkanethiols tend to desorb at potentials outside the potential window defined by 800 to −1400 mV (vs Ag/AgCl) (Walczak et al., 1991, Widrig et al., 1991) and at temperatures over 100° C. (Bhatia and Garrison, 1997). Also, the gold/thiol junction generates a significant tunneling barrier (−2 eV) (Ranganathan et al., 2001). Alkoxy-terminated silanes can react with surface hydroxyl groups on metal-oxide electrodes to form a polysiloxane linkage (Curran et al., 2005, Quan et al., 2004). However, Kraft has reported that metal oxide substrates are not stable during anodic potential cycling, due to the anodic dissolution of the metal-oxide coating (Kraft et al., 1994).

SUMMARY OF THE INVENTION

In accordance with certain aspects of the invention, there is provided a bioelectronic device comprising an electrically conductive carbon electrode and a bioelectronic interface that is bonded to a surface of the electrically conductive carbon electrode, wherein the interface includes a catalytically active material that facilitates electron transfer, and wherein the catalytically active material is electrostatically bound directly or indirectly to the electrically conductive carbon electrode, thereby facilitating easy removal and replacement of components of the interface that may become degraded during use.

In accordance with other aspects of the invention, a process for reconstituting a bioelectronic interface of a bioelectronic device is provided. The process includes providing a bioelectronic device having an electrically conductive carbon electrode and a bioelectronic interface that includes catalytically active material, and which is electrostatically bound directly or indirectly to a surface of the electrically conductive carbon electrode, and thereafter exposing the bioelectronic interface to an aqueous medium having a pH that releases the catalytically active material from the surface of the electrically conductive carbon electrode, then exposing the electrically conductive carbon electrode to an aqueous medium that has a second pH that facilitates electrostatic bonding of a catalytically active material to the surface of the electrically conductive carbon electrode; and introducing fresh catalytically active material to the aqueous medium, and electrostatically bonding the fresh catalytically active material to the surface of the electrically conductive carbon electrode, thereby renewing the interface.

Certain aspects of the invention provide a relatively simple method by which the bioelectronic interface is renewed (immersing the electrode sequentially in multiple solutions, each of which contains soluble reactants that are added to the interface) and may offer a major advantage for bioreactor operation. Specifically, the carbon electrodes (e.g., reticulated vitreous carbon) could have the old interface removed and a new one installed without removing the electrodes from the reactor. The approach would involve flowing appropriate solutions through the reactor. This feature might preclude the need to remove the carbon electrodes from the reactor, processing them, and then returning them to the reactor each time the enzyme needs to be replaced.

In accordance with a further aspect of the invention, an electrobiocatalytic reactor includes a cathode compartment containing a first electrolytic solution and an anode component compartment containing a second electrolytic solution, wherein the anode compartment and the cathode compartment are separated by a proton-permeable membrane; a cathode located at the cathode compartment and in contact with the first electrolyte, and an anode located at the anode compartment and in contact with the second electrolyte, wherein at least one of the anode and cathode is an electrically conductive carbon electrode; and a bioelectronic interface bonded to a surface of at least one electrically conductive carbon electrode, wherein the bioelectronic interface includes a catalytically active material that facilitates electron transfer, and wherein the catalytically active material is electrostatically bound directly or indirectly to the electrically conductive carbon electrode. As is understood by those having ordinary skill in the art, such electrobiocatalytic reactors are configurable for use as biosensors for detecting and/or quantifying analytes, for use in conducting chemical reactions to form a desired product or degrade an undesirable compound, or for use as a biofuel cell.

The bioelectronic interface in accordance with certain aspects of the invention is assembled layer by layer, by alternately immersing the electrode in solutions containing polyelectrolytes having opposite charges. Because each polyelectrolyte layer added to the interface contributes a thickness of about one to five nanometers, this approach provides excellent control over the thickness of the bioelectronic interface. Such control is not possible for other types of immobilization schemes. In both our experimental and modeling work, we observed the interface developed using known techniques was either too thick or too thin and the reaction rate was low. Our approach, which enables us to assemble the optimum, thickness by controlling how many bioelectronic cassettes we assemble, provides a facile method to achieve the optimal interface thickness.

These and other features, advantages and objects of the present invention will be further understood and appreciated by those skilled in the art by reference to the following specification, claims and appended drawings.

DESCRIPTION OF THE PREFERRED EMBODIMENTS

Figure 1:
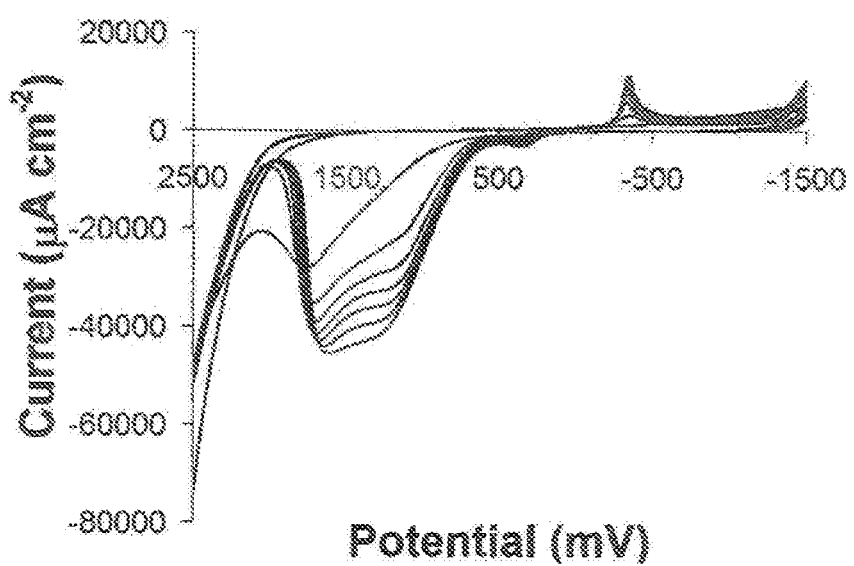
FIG. 1 is a cyclic voltammogram for the preparation of a Gly-modified GCE. Scan Rate 100 mV s$^{-1}$; supporting electrolyte: phosphate buffer solution (pH 7.4).

One aspect of the present invention is a unique bioelectronic interface that holds an electron mediator, cofactor, and enzyme to an electrically conductive carbon electrode (such as a glassy carbon electrode-GCE) in a molecular orientation that allows multistep electron transfer between the enzyme and electrode. Interface fabrication is based on molecular self-assembly via reversible, pH-dependent ionic interactions, allowing the cofactor and enzyme to be removed via a change in pH, and then replaced to regenerate the biocatalytic activity.

Another aspect of the present invention is a biocatalytic reactor including one or more electrodes having bioelectronic interfaces fabricated according to the unique processes described herein. The electrodes may comprise a carbon substrate having a renewable bioelectronic interface.

Another aspect of the present invention is a method of designing and/or optimizing a biocatalytic reactor or other device including a bioelectronic interface. The method includes using a mathematical model that describes bioelectronic interfaces containing reversible enzymes, cofactors, and mediators.

As used herein, the term "bioelectronic device" refers to any device having an electrode with a bioelectronic interface used to facilitate an electrochemical reaction.

The term "bioelectronic interface" refers to an interface containing a biochemically active substance, and which is assembled on an inorganic electrode surface to facilitate a biochemically mediated electrochemical reaction.

The term "catalytically active material" refers to a material that initiates or accelerates an electrochemical reaction without itself being consumed, although some degradation may occur in non-stoichiometric proportion. Catalytically active materials include, but are not necessarily limited to, enzymes.

The term "electrostatically bound" is used herein to refer to a bond formed by the attraction of oppositely charged ions.

The term "ionic moiety" refers to an atom or group of atoms that is ionic or capable of being ionized.

The term "polyelectrolyte" refers to a molecule, typically a large molecule, but not necessarily a polymer, having a plurality of ionizing moieties.

The term "linking moiety" refers to a group of atoms bound together, which reacts with a carbon atom or some other atom on the surface of an electrically conductive carbon electrode to form a covalent bond (e.g., a carbon-nitrogen bond), whereby the substance containing the linking moiety is bound to the carbon electrode.

The term "ionic linker" refers to a molecule or substance that contains at least one linking moiety, which binds the ionic linker to a conductive carbon electrode, and at least one ionic moiety(s), which enables other substances to be electrostatically bound to the ionic linker.

The term, "proton permeable membrane" refers to a semi-permeable membrane that selectively transports protons (actually hydronium ions) while being impermeable to the products and reactants of an electrochemical reaction.

An electrobiocatalytic reactor (FIG. 1A) according to an aspect of the present invention includes a vessel or container 2 containing one or more conductive electrodes 3A and 3B onto which a bioelectronic interface is attached. The electrode(s) are preferably made of a conductive carbon material. In the illustrated example, the reactor 1 includes a cathode compartment 4 and anode compartment 5 that are separated by an optional proton permeable membrane 6. Reactor 1 may be utilized to simultaneously carry out a reduction reaction in the cathode compartment 4 and an oxidation reaction in the anode compartment 5. In some applications, a proton permeable membrane is not needed, and the anode and cathode are present in the same compartment.

According to one aspect of the present invention, alcohols are produced in the cathode compartment 4 from ketones or aldehydes, and ketones or aldehydes are produced in the anode compartment 5 from alcohols. Protons ($H^+$) produced by the oxidation reaction at the anode pass through the proton-permeable membrane 6, and are consumed by the reduction reaction at the cathode. Electrons generated by the oxidation reaction at the anode are delivered to the cathode through an external electrical circuit 10, and are consumed by the reduction reaction at the cathode.

According to one aspect of the present invention, bioreactor 1 (FIG. 1A) may be configured to produce mannitol from glucose in the cathode compartment 4 using the enzymes xylose isomerase (XI) and mannitol dehydrogenase (MtDH). Simultaneously, the bioreactor 1 may produce dihydroxyacetone from glycerol in the anode compartment 4 using enzyme glycerol dehydrogenase. When the bioreactor 1 is configured in this way, an aqueous glucose solution flows into the cathode compartment 4, where it contacts a carbon electrode 3A (the cathode) that is coated with a bioelectronic interface containing both MtDH and XI. Examples of bioelectronic interfaces and methods of fabricating such interfaces are described in more detail below. The XI converts the glucose to fructose, which is then converted into mannitol by the MtDH. Electrons consumed in the second reaction are transferred from the cathode 3A to the MtDH enzyme. An electron mediator (e.g., toluidine blue O) and/or a cofactor (e.g., NADH) may be used to facilitate electron transfer between the cathode 3A and the MtDH. At the same time, an aqueous glycerol solution 8 flows into the anode compartment 5, where it contacts a second carbon electrode 3B (the anode) that is coated with a bioelectronic interface containing glycerol dehydrogenase. The glycerol dehydrogenase oxidizes the glycerol to dihydroxyacetone. Electrons produced in this reaction are transferred from the glycerol dehydrogenase to the anode 3B. An electron mediator (e.g. toluidine blue O) and/or a cofactor (e.g., NADH) may be used to facilitate electron transfer between the glycerol dehydrogenase and the anode 3B.

Bioreactor 1 may be configured in a variety of ways. A wide variety of reactants and redox enzymes may be substituted to form many different products. Enzymes are commonly classified using nomenclature based on Enzyme Commission (EC) number. The present invention applies to several types of oxidoreductases (EC1). Numerous EC1s are listed in Table 1. Transferases, transaminases, hydrolases, lyases, isomerases, and ligases that may be employed in combination with the oxidoreductases are also listed in Table 1.

TABLE 1

| EC Number | Chemical Name |
|---|---|
| OXIDOREDUCTASES | |
| 1.1.1.1 | Alcohol dehydrogenase |
| 1.1.1.3 | Homoserine dehydrogenase |
| 1.1.1.8 | Glycerol-3-phosphate dehydrogenase |

TABLE 1-continued

| EC Number | Chemical Name |
|---|---|
| 1.1.1.9 | D-Xylulose reductase |
| 1.1.1.10 | l-Xylulose reductase |
| 1.1.1.14 | l-Iditol dehydrogenase |
| 1.1.1.19 | Glucuronate reductase |
| 1.1.1.21 | Aldehyde reductase |
| 1.1.1.22 | UDPglucose dehydrogenase |
| 1.1.1.23 | Histidinol dehydrogenase |
| 1.1.1.25 | Shikimate dehydrogenase |
| 1.1.1.27 | Lactate dehydrogenase |
| 1.1.1.29 | Glycerate dehydrogenase |
| 1.1.1.30 | 3-Hydroxybutyrate dehydrogenase |
| 1.1.1.31 | 3-Hydroxyisobutyrate dehydrogenase |
| 1.1.1.32 | Mevaldate reductase |
| 1.1.1.34 | Hydroxymethylglutaryl-CoA reductase (NADPH) |
| 1.1.1.35 | 3-Hydroxyacyl-CoA dehydrogenase |
| 1.1.1.37 | Malate dehydrogenase |
| 1.1.1.39 | Malate dehydrogenase (decarboxylating) |
| 1.1.1.41 | Isocitrate dehydrogenase (NAD+) |
| 1.1.1.44 | Phosphogluconate dehydrogenase (decarboxylating) |
| 1.1.1.45 | l-Gulonate dehydrogenase |
| 1.1.1.49 | Glucose-6-phosphate dehydrogenase |
| 1.1.1.56 | Ribitol dehydrogenase |
| 1.1.1.79 | Glyoxylate reductase (NADP+) |
| 1.1.1.81 | Hydroxypyruvate reductase |
| 1.1.1.82 | Malate dehydrogenase (NADP+) |
| 1.1.1.85 | 3-Isopropylmalate dehydrogenase |
| 1.1.1.86 | Ketol-acid reductoisomerase |
| 1.1.1.95 | Phosphoglycerate dehydrogenase |
| 1.1.1.100 | 3-Oxoacyl-[acyl-carrier-protein] reductase |
| 1.1.1.102 | 3-Dehydrosphinganine reductase |
| 1.1.1.105 | Retinol dehydrogenase |
| 1.1.1.130 | 3-Dehydro-L-gulonate 2-dehydrogenase |
| 1.1.1.157 | 3-Hydroxybutyryl-CoA dehydrogenase |
| 1.1.1.158 | UDP-N-acetylmuramate dehydrogenase |
| 1.1.1.169 | 2-Dehydropantoate 2-reductase |
| 1.1.1.204 | Xanthine dehydrogenase |
| 1.1.1.205 | IMP-dehydrogenase |
| 1.1.3.8 | l-Gulonolactone oxidase |
| 1.1.3.22 | Xanthine oxidase |
| 1.1.99.1 | Choline dehydrogenase |
| 1.1.99.5 | Glycerol-3-phosphate dehydrogenase |
| 1.2.1.3 | Aldehyde dehydrogenase (NAD+) |
| 1.2.1.7 | Benzaldehyde dehydrogenase (NADP+) |
| 1.2.1.8 | Betaine-aldehyde dehydrogenase |
| 1.2.1.11 | Aspartate-semialdehyde dehydrogenase |
| 1.2.1.12 | Glyceraldehyde-3-phosphate dehydrogenase |
| 1.2.1.13 | Glyceraldehyde-3-phosphate dehydrogenase |
| 1.2.1.16 | Succinate-semialdehyde dehydrogenase (NAD(P)+) |
| 1.2.1.18 | Malonate semialdehyde dehydrogenase (acetylating) |
| 1.2.1.21 | Glycolaldehyde dehydrogenase |
| 1.2.1.23 | 2-Oxoaldehyde dehydrogenase (NAD+) |
| 1.2.1.24 | Succinate semialdehyde dehydrogenase |
| 1.2.1.25 | 2-Oxoisovalerate dehydrogenase (acylating) |
| 1.2.1.27 | Methylmalonate-semialdehyde dehydrogenase (acylating) |
| 1.2.1.31 | l-Aminoadipate-semialdehyde dehydrogenase |
| 1.2.1.32 | Aminomuconate-semialdehyde dehydrogenase |
| 1.2.1.36 | Retinal dehydrogenase |
| 1.2.1.41 | Glutamate-5-semialdehyde dehydrogenase |
| 1.2.1.52 | Oxoglutarate dehydrogenase |
| 1.2.3.5 | Glyoxylate oxidase |
| 1.2.3.7 | Indole-3-acetaldehyde oxidase |
| 1.2.4.1 | Pyruvate dehydrogenase (lipoamide) |
| 1.2.4.2 | Oxoglutarate dehydrogenase (lipoamide) |
| 1.2.7.1 | Pyruvate synthase |
| 1.2.7.2 | 2-Oxobutyrate synthase |
| 1.3.1.1 | Dihydrouracil dehydrogenase (NAD+) |
| 1.3.1.2 | Dihydropyrimidine dehydrogenase (NADP+) |
| 1.3.1.8 | Acyl-CoA dehydrogenase (NADP+) |
| 1.3.1.9 | Enoyl-[acyl-carrier-protein] reductase (NADH) |
| 1.3.1.10 | Enoyl-[acyl-carrier-protein] reductase (NADPH, B-specific) |
| 1.3.1.13 | Prephenate dehydrogenase (NADP+) |
| 1.3.1.14 | Orotate reductase (NADH) |
| 1.3.1.26 | Dihydrodipicolinate reductase |
| 1.3.1.35 | Phosphatidylcholine desaturase |
| 1.3.3.3 | Coproporphyrinogen oxidase |
| 1.3.3.4 | Protoporphyrinogen oxidase |
| 1.3.5.1 | Succinate dehydrogenase (ubiquinone) |
| 1.3.99.1 | Succinate dehydrogenase |
| 1.3.99.2 | Butyryl-CoA dehydrogenase |
| 1.3.99.3 | Acyl-CoA dehydrogenase |
| 1.3.99.7 | Glutaryl-CoA dehydrogenase |
| 1.3.99.10 | Isovaleryl-CoA dehydrogenase |
| 1.4.1.1 | Alanine dehydrogenase |
| 1.4.1.2 | Glutamate dehydrogenase |
| 1.4.1.7 | Serine dehydrogenase |
| 1.4.1.8 | Valine dehydrogenase (NADP+) |
| 1.4.1.9 | Leucine dehydrogenase |
| 1.4.1.10 | Glycine dehydrogenase |
| 1.4.1.14 | Glutamate synthase (NADH) |
| 1.4.1.19 | Tryptophan dehydrogenase |
| 1.4.3.1 | d-Aspartate oxidase |
| 1.4.3.2 | l-Amino-acid oxidase |
| 1.4.3.4 | Amine oxidase (flavin-containing) |
| 1.4.3.8 | Ethanolamine oxidase |
| 1.4.4.2 | Glycine dehydrogenase (decarboxylating) |
| 1.5.1.2 | Pyrroline-5-carboxylate reductase |
| 1.5.1.3 | Dihydrofolate reductase |
| 1.5.1.5 | Methylenetetrahydrofolate reductase (NADP+) |
| 1.5.1.6 | Formyltetrahydrofolate dehydrogenase |
| 1.5.1.7 | Saccharopine dehydrogenase (NAD+, L-lysine-forming) |
| 1.5.1.8 | Saccharopine dehydrogenase (NADP+, L-lysine-forming) |
| 1.5.1.9 | Saccharopine dehydrogenase (NAD+, L-glutamate-forming) |
| 1.5.1.10 | Saccharopine dehydrogenase (NADP+, L-glutamate-forming) |
| 1.5.1.12 | 1-Pyrroline-5-carboxylate dehydrogenase |
| 1.5.3.1 | Sarcosine oxidase |
| 1.5.99.1 | Sarcosine dehydrogenase |
| 1.5.99.2 | Dimethylglycine dehydrogenase |
| 1.5.99.8 | Proline dehydrogenase |
| 1.6.4.1 | Cystine reductase (NADH) |
| 1.6.5.3 | NADH dehydrogenase (ubiquinone) |
| 1.6.6.1 | Nitrate reductase (NADH) |
| 1.6.6.2 | Nitrate reductase [NAD(P)H] |
| 1.6.6.3 | Nitrate reductase (NADPH) |
| 1.6.6.4 | Nitrite reductase [NAD(P)H] |
| 1.6.6.8 | GMP reductase |
| 1.7.3.3 | Urate oxidase |
| 1.7.7.1 | Ferredoxin-nitrate reductase |
| 1.7.99.4 | Nitrate reductase |
| 1.8.1.3 | Hypotaurine dehydrogenase |
| 1.8.1.4 | Dihydrolipoamide dehydrogenase |
| 1.8.2.1 | Sulfite dehydrogenase |
| 1.8.3.1 | Sulfite oxidase |
| 1.8.7.1 | Sulfite reductase (ferredoxin) |
| 1.8.99.1 | Sulfite reductase |
| 1.8.99.2 | Adenylsulphate reductase |
| 1.9.3.1 | Cytochrome-c oxidase |
| 1.10.2.1 | l-Ascorbate-cytochrome-b5 reductase |
| 1.10.2.2 | Ubiquinol-cytochrome-c reductase |
| 1.10.3.3 | l-Ascorbate oxidase |
| 1.10.99.1 | Plastoquinol-plastocyanin reductase |
| 1.13.11.1 | Catechol 1,2-dioxygenase |
| 1.13.11.2 | Catechol 2,3-dioxygenase |
| 1.13.11.5 | Homogentisate 1,2-dioxygenase |
| 1.13.11.6 | 3-Hydroxyanthranilate 3,4-dioxygenase |
| 1.13.11.11 | Tryptophan 2,3-dioxygenase |
| 1.13.11.20 | Cysteine dioxygenase |
| 1.13.11.21 | β-Carotene 15,154-dioxygenase |
| 1.13.11.27 | 4-Hydroxyphenylpyruvate dioxygenase |
| 1.13.11.34 | Arachidonate 5-lipoxygenase |
| 1.13.99.1 | myo-Inositol oxygenase |
| 1.14.11.1 | g-Butyrobetaine dioxygenase |
| 1.14.11.2 | Procollagen-proline dioxygenase |
| 1.14.11.8 | Trimethyllysine dioxygenase |
| 1.14.12.1 | Anthranilate 1,2-dioxygenase (deaminating, decarboxylating) |
| 1.14.13.5 | Imidazoleacetate 4-monooxygenase |
| 1.14.13.9 | Kynurenine 3-monooxygenase |
| 1.14.13.11 | trans-Cinnamate 4-monooxygenase |
| 1.14.13.12 | Benzoate 4-monooxygenase |
| 1.14.13.39 | Nitric oxide synthase |
| 1.14.16.1 | Phenylalanine 4-monooxygenase |
| 1.14.16.2 | Tyrosine 3-monooxygenase |
| 1.14.16.4 | Tryptophan 5-monooxygenase |
| 1.14.17.1 | Dopamine β-monooxygenase |
| 1.14.18.1 | Monophenol monooxygenase |

TABLE 1-continued

| EC Number | Chemical Name |
|---|---|
| 1 14.99.1 | Prostaglandin synthase |
| 1 14.99.5 | Stearoyl-CoA desaturase |
| 1.14.99.7 | Squalene monooxygenase |
| 1.14.99.25 | Linoleoyl-CoA desaturase |
| 1.17.4.1 | Ribonucleoside-diphosphate reductase |
| 1.18.6.1 | Nitrogenase |
| | TRANSFERASES |
| 2.1.1.1 | Nicotinamide N-methyltransferase |
| 2.1.1.2 | Guanidinoacetate N-methyltransferase |
| 2.1.1.3 | Thetin-homocysteine S-methyltransferase |
| 2.1.1.4 | Acetylserotonin N-methyltransferase |
| 2.1.1.5 | Betaine-homocysteine S-methyltransferase |
| 2.1.1.6 | Catechol O-methyl transferase |
| 2.1.1.10 | Homocysteine S-methyltransferase |
| 2.1.1.13 | 5-Methyltetrahydrofolate-homocysteine S-methyl transferase |
| 2.1.1.14 | 5-Methyltetrahydropteroyltriglutamate homocysteine S-methyltransferase |
| 2.1.1.17 | Phosphatidylethanolamine N-methyltransferase |
| 2.1.1.20 | Glycine N-methyltransferase |
| 2.1.1.28 | Phenylethanolamine N-methyltransferase |
| 2.1.1.45 | Thymidylate synthase |
| 2.1.1.71 | Phosphatidyl-N-methylethanolamine N-methyltransferase |
| 2.1.2.1 | Glycine hydroxymethyltransferase |
| 2.1.2.2 | Phosphoribosylglycinamide formyltransferase |
| 2.1.2.3 | Phosphoribosylaminoimidazole carboxamide formyltransferase |
| 2.1.2.5 | Glutamate formiminotransferase |
| 2.1.2.10 | Aminomethyl transferase |
| 2.1.3.1 | Methylmalonyl-CoA carboxyltransferase |
| 2.1.3.2 | Aspartate carbamoyltransferase |
| 2.1.3.3 | Ornithine carbamoyltransferase |
| 2.1.4.1 | Glycine amidinotransferase |
| 2.2.1.1 | Transketolase |
| 2.2.1.2 | Transaldolase |
| 2.3.1.1 | Amino-acid N-acetyltransferase |
| 2.3.1.4 | Glucosamine-phosphate N-acetyltransferase |
| 2.3.1.5 | Arylamine N-acetyltransferase |
| 2.3.1.6 | Choline O-acetyltransferase |
| 2.3.1.7 | Carnitine O-acetyltransferase |
| 2.3.1.8 | Phosphate acetyltransferase |
| 2.3.1.9 | Acetyl-CoA C-acetyltransferase |
| 2.3.1.12 | Dihydrolipoamide S-acetyltransferase |
| 2.3.1.15 | Glycerol-3-phosphate O-acyltransferase |
| 2.3.1.16 | Acetyl-CoA C-acyltransferase |
| 2.3.1.20 | Diacylglycerol O-acyltransferase |
| 2.3.1.23 | Lysolecithin acyltransferase |
| 2.3.1.24 | Sphingosine N-acyltransferase |
| 2.3.1.30 | Serine O-acetyltransferase |
| 2.3.1.37 | 5-Aminolevulinate synthase |
| 2.3.1.38 | [Acyl-carrier-protein] S-acetyltransferase |
| 2.3.1.39 | [Acyl-carrier-protein] S-malonytransferase |
| 2.3.1.41 | 3-Oxoacyl-[acyl-carrier-protein] synthase |
| 2.3.1.46 | Homoserine O-succinyltransferase |
| 2.3.1.50 | Serine C-palmitoyltransferase |
| 2.3.1.51 | 1-Acylglycerol-3-phosphate O-acyltransferase |
| 2.3.1.76 | Retinol O-fatty-acyltransferase |
| 2.4.1.1 | Phosphorylase |
| 2.4.1.9 | Inulosucrase |
| 2 4.1.11 | Glycogen (starch) synthase |
| 2.4.1.13 | Sucrose synthase |
| 2.4.1.16 | Chitin synthase |
| 2.4.1.17 | Glucuranosyltransferase |
| 2.4.1.21 | Starch synthase |
| 2.4.1.22 | Lactose synthase |
| 2.4.1.23 | Sphingosine β-galactosyltransferase |
| 2.4.1.29 | Cellulose synthase (GDP-forming) |
| 2.4.1.32 | Glucomannan 4-β-mannosyltransferase |
| 2.4.1.33 | Alginate synthase |
| 2.4.1.47 | Acylsphingosine galactosyltransferase |
| 2.4.1.62 | Ganglioside galactosyltransferase |
| 2.4.1.68 | Glycoprotein 6-a-L-fucosyltransferase |
| 2.4.1.69 | Galactoside 2-a-L-fucosyltransferase |
| 2.4.2.1 | Purine-nucleoside phosphorylase |
| 2.4.2.2 | Pyrimidine-nucleoside phosphorylase |
| 2.4.2.4 | Thymidine phosphorylase |
| 2.4.2.8 | Hypoxanthine phosphoribosyltransferase |

TABLE 1-continued

| EC Number | Chemical Name |
|---|---|
| 2.4.2.9 | Uracil phosphoribosyltransferase |
| 2.4.2.10 | Orotate phosphoribosyltransferase |
| 2.4.2.11 | Nicotinate phosphoribosyltransferase |
| 2.4.2.14 | Amidophosphoribosyltransferase |
| 2.4.2.15 | Guanosine phosphorylase |
| 2.4.2.17 | ATP phosphoribosyltransferase |
| 2.4.2.18 | Anthranilate phosphoribosyltransferase |
| 2.4.2.19 | Nicotinate-nucleotide pyrophosphorylase (carboxylating) |
| 2.4.99.1-11 | Sialyltransferases |
| 2.4.99.7 | Sialyltransferase |
| 2.5.1.1 | Dimethylallyltranstransferase |
| 2.5.1.6 | Methionine adenosyltransferase |
| 2.5.1.10 | Geranyltranstransferase |
| 2.5.1.16 | Spermidine synthase |
| 2.5.1.19 | 3-Phosphoshikimate 1-carboxyvinyl-transferase |
| 2.5.1.21 | Farnesyltransferase |
| 2.5.1.22 | Spermine synthase |
| 2.5.1.29 | Farnesyltranstransferase |
| 2.5.1.32 | Geranylgeranyl-diphosphate geranylgeranyl transferase |
| | TRANSAMINASES |
| 2.6.1.1 | Aspartate transaminase |
| 2.6 1.2 | Alanine transaminase |
| 2.6.1.4 | Glycine transaminase |
| 2.6 1.5 | Tyrosine transaminase |
| 2.6 1.6 | Leucine transaminase |
| 2.6.1.9 | Histidinol-phosphate transaminase |
| 2.6.1.13 | Ornithine-oxo-acid transaminase |
| 2.6.1.16 | Glutamine-fructose-6-phosphate transaminase |
| 2.6.1.17 | Succinyldiaminopimelate transaminase |
| 2.6.1.18 | β-Alanine-pyruvate transaminase |
| 2.6.1.19 | 4-Aminobutyrate transaminase |
| 2.6.1.22 | l-3-Aminoisobutyrate transaminase |
| 2.6.1.23 | 4-Hydroxyglutamate transaminase |
| 2.6.1.27 | Tryptophan transaminase |
| 2.6.1.32 | Valine-3-methyl-2-oxovalerate transaminase |
| 2.6.1.36 | l-Lysine 6-transaminase |
| 2.6.1.39 | 2-Aminoadipate transaminase |
| 2.6.1.42 | Branched-chain-amino-acid transaminase |
| 2.6.1.44 | Alanine-glyoxylate transaminase |
| 2.6.1.51 | Serine-pyruvate transaminase |
| 2.6.1.52 | Phosphoserine transaminase |
| 2.6.1.66 | Valine-pyruvate transaminase |
| 2.7.1.1 | Hexokinase |
| 2.7.1.2 | Glucokinase |
| 2.7.1.3 | Ketohexokinase |
| 2.7.1.4 | Fructokinase |
| 2.7.1.6 | Galactokinase |
| 2.7.1.7 | Mannokinase |
| 2.7.1.11 | 6-Phosphofructokinase |
| 2.7.1.15 | Ribokinase |
| 2.7.1.16 | Ribulokinase |
| 2.7.1.17 | Xylulokinase |
| 2.7.1.19 | Phosphoribulokinase |
| 2.7.1.24 | Dephospho-CoA kinase |
| 2.7.1.25 | Adenylylsulfate kinase |
| 2.7.1.28 | Triokinase |
| 2.7.1.30 | Glycerol kinase |
| 2.7.1.31 | Glycerate kinase |
| 2.7.1.32 | Choline kinase |
| 2.7.1.33 | Pantothenate kinase |
| 2.7.1.34 | Pantetheine kinase |
| 2.7.1.36 | Mevalonate kinase |
| 2.7.1.39 | Homoserine kinase |
| 2.7.1.40 | Pyruvate kinase |
| 2.7 1.47 | D-Ribulokinase |
| 2.7.1.53 | l-Xylulokinase |
| 2.7.1.60 | N-Acylmannosamine kinase |
| 2.7.1.71 | Shikimate kinase |
| 2.7.1.80 | Pyrophosphate-serine phosphotransferase |
| 2.7.1.82 | Ethanolamine kinase |
| 2.7.1.107 | Diacylglycerol kinase |
| 2.7.2.3 | Phosphoglycerate kinase |
| 2.7.2.4 | Aspartate kinase |
| 2.7.2.6 | Formate kinase |
| 2.7.2.11 | Glutamate 5-kinase |
| 2.7.3.2 | Creatine kinase |
| 2.7.4.2 | Phosphomevalonate kinase |

TABLE 1-continued

| EC Number | Chemical Name |
|---|---|
| 2.7.4.3 | Adenylate kinase |
| 2.7.4.4 | Nucleoside-phosphate kinase |
| 2.7.4.6 | Nucleoside-diphosphate kinase |
| 2.7.4.8 | Guanylate kinase |
| 2.7.4.9 | dtmp kinase |
| 2.7.4.14 | Cytidylate kinase |
| 2.7.6.1 | Ribose-phosphate pyrophosphokinase |
| 2.7.7.3 | Pantetheine-phosphate adenylyltransferase |
| 2.7.7.4 | Sulfate adenylyl transferase |
| 2.7.7.6 | RNA nucleotidyltransferase (DNA-directed) |
| 2.7.7.7 | DNA nucleotidyltransferase (DNA-directed) |
| 2.7.7.9 | UTP-glucose-1-phosphate uridylyltransferase |
| 2.7.7.10 | UTP-hexose-1-phosphate uridylyltransferase |
| 2.7.7.12 | UDP glucose-hexose-1-phosphate uridylyltransferase |
| 2.7.7.13 | Mannose-1-phosphate guanylyltransferase |
| 2.7.7.14 | Ethanolamine-phosphate cytidylyltransferase |
| 2.7.7.15 | Choline-phosphate cytidylyltransferase |
| 2.7.7.18 | Nicotinate-nucleotide adenylyltransferase |
| 2.7.7.23 | UDP-N-acetylglucosamine pyrophorylase |
| 2.7.7.24 | Glucose-1-phosphate thymidylyltransferase |
| 2.7.7.27 | Glucose-1-phosphate adenylyltransferase |
| 2.7.7.34 | Glucose-1-phosphate guanylyltransferase |
| 2.7.7.41 | Phosphatidate cytidylyltransferase |
| 2.7.7.43 | N-Acylneuraminate cytidylyltransferase |
| 2.7.8.1 | Ethanolamine phosphotransferase |
| 2.7.8.2 | Diacylglycerol cholinephosphotransferase |
| 2.7.8.3 | Ceramide cholinephosphotransferase |
| 2.7.8.5 | CDPdiacylglycerol-glycerol-3-phosphate 3-phosphatidyltransferase |
| 2.7.8.8 | CDPdiacylglycerol-serine O-phosphatidyltransferase |
| 2.7.8.11 | CDPdiacylglycerol-inositol 3-phosphatidyltransferase |
| 2.8.3.5 | 3-Oxoacid CoA-transferase |
| 2.8.3.6 | 3-Oxoadipate CoA-transferase |
| HYDROLASES | |
| 3.1.1.3 | Triacylglycerol lipase |
| 3.1.1.4 | Phospholipase A2 |
| 3.1.1.5 | Lysophospholipase |
| 3.1.1.7 | Acetylcholinesterase |
| 3.1.1.17 | Gluconolactonase |
| 3.1.1.21 | Retinyl-palmitate esterase |
| 3.1.1.28 | Acylcarnitine hydrolase |
| 3.1.1.31 | 6-Phosphogluconolactonase |
| 3.1.1.32 | Phospholipase A1 |
| 3.1.2.1 | Acetyl-CoA hydrolase |
| 3.1.2.3 | Succinyl-CoA hydrolase |
| 3.1.2.4 | 3-Hydroxyisobutyryl-CoA hydrolase |
| 3.1.2.11 | Acetoacetyl-CoA hydrolase |
| 3.1.2.20 | Acyl-CoA hydrolase |
| 3.1.3.2 | Acid phosphatase |
| 3.1.3.3 | Phosphoserine phosphatase |
| 3.1.3.4 | Phosphatidate phosphatase |
| 3.1.3.5 | 54-Nucleotidase |
| 3.1.3.9 | Glucose-6-phosphatase |
| 3.1.3.11 | Fructose-bisphosphatase |
| 3.1.3.15 | Histidinol-phosphatase |
| 3.1.3.25 | myo-Inositol-1(or 4)-monophosphatase |
| 3.1.3.27 | Phosphatidylglycerophosphatase |
| 3.1.3.29 | N-Acylneuraminate-9-phosphatase |
| 3.1.3.31 | Nucleotidase |
| 3.1.4.2 | Glycerophosphocholine phosphodiesterase |
| 3.1.4.3 | Phospholipase C |
| 3.1.4.4 | Phospholipase D |
| 3.1.4.10 | 1-Phosphatidylinositol phosphodieterase |
| 3.1.4.12 | Sphingomyelin phosphodiesterase |
| 3.2.1.21 | β-Glucosidase |
| 3.2.1.23 | β-Galactosidase |
| 3.2.1.26 | β-Fructofuranosidase |
| 3.2.1.45 | Glucosylceramidase |
| 3.2.1.46 | Galactosylceramidase |
| 3.2.1.48 | Sucrose α-glucosidase |
| 3.2.2.2 | Inosine nucleosidase |
| 3.3.1.1 | Adenosylhomocysteinase |
| 3.5.1.1 | Asparaginase |
| 3.5.1.2 | Glutaminase |
| 3.5.1.6 | β-Ureidopropionase |
| 3.5.1.9 | Arylformamidase |
| 3.5.1.18 | Succinyl-diaminopimelate desuccinylase |

TABLE 1-continued

| EC Number | Chemical Name |
|---|---|
| 3.5.1.22 | Pantothenase |
| 3.5.1.23 | Ceramidase |
| 3.5.2.2 | Dihydropyrimidinase |
| 3.5.2.3 | Dihydroorotase |
| 3.5.2.5 | Allantoinase |
| 3.5.2.7 | Imidazolonepropionase |
| 3.5.2.10 | Creatininase |
| 3.5.3.1 | Arginase |
| 3.5.3.4 | Allantoicase |
| 3.5.3.6 | Arginine deiminase |
| 3.5.4.1 | Cytosine deaminase |
| 3.5.4.3 | Guanine deaminase |
| 3.5.4.6 | AMP deaminase |
| 3.5.4.10 | IMP cyclohydrolase |
| 3.5.4.12 | dCMP deaminase |
| 3.5.4.19 | Phosphoribosyl-AMP cyclohydrolase |
| 3.6.1.3 | Adenosinetriphosphatase |
| 3.6.1.15 | Nucleoside-triphosphatase |
| 3.6.1.31 | Phosphoribosyl-ATP pyrophosphatase |
| 3.6.1.34 | H+-transporting ATP synthase |
| 3.7.1.2 | Fumarylacetoacetase |
| 3.7.1.3 | Kynureninase |
| 3.9.1.1 | Phosphoamidase |
| LYASES | |
| 4.1.1.1 | Pyruvate decarboxylase |
| 4.1.1.3 | Oxaloacetate decarboxylase |
| 4.1.1.4 | Acetoacetate decarboxylase |
| 4.1.1.9 | Malonyl-CoA decarboxylase |
| 4.1.1.11 | Aspartate 1-decarboxylase |
| 4.1.1.12 | Aspartate 4-decarboxylase |
| 4.1.1.15 | Glutamate decarboxylase |
| 4.1.1.17 | Ornithine decarboxylase |
| 4.1.1.20 | Diaminopimelate decarboxylase |
| 4.1.1.21 | Phosphoribosylaminoimidazole carboxylase |
| 4.1.1.22 | Histidine decarboxylase |
| 4.1.1.23 | Orotidine-5'-phosphate decarboxylase |
| 4.1.1.25 | Tyrosine decarboxylase |
| 4.1.1.28 | Aromatic-L-amino-acid decarboxylase |
| 4.1.1.29 | Sulfoalanine decarboxylase |
| 4.1.1.32 | Phosphoenolpyruvate carboxykinase (GTP) |
| 4.1.1.33 | Diphosphomevalonate decarboxylase |
| 4.1.1.34 | Dehydro-l-gulonate decarboxylase |
| 4.1.1.36 | Phosphopantothenoylcysteine decarboxylase |
| 4.1.1.37 | Uroporphyrinogen decarboxylase |
| 4.1.1.39 | Ribulose-bisphosphate carboxylase |
| 4.1.1.41 | Methylmalonyl-CoA decarboxylase |
| 4.1.1.43 | Phenylpyruvate decarboxylase |
| 4.1.1.45 | Aminocarboxymuconate-semialdehyde decarboxylase |
| 4.1.1.48 | Indole-3-glycerol-phosphate synthase |
| 4.1.1.49 | Phosphoenolpyruvate carboxykinase (ATP) |
| 4.1.1.50 | Adenosylmethionine decarboxylase |
| 4.1.1.65 | Phosphatidylserine decarboxylase |
| 4.1.1.71 | 2-Oxoglutarate decarboxylase |
| 4.1.2.5 | Threonine aldolase |
| 4.1.2.12 | Ketopantoaldolase |
| 4.1.2.13 | Fructose-bisphosphate aldolase |
| 4.1.2.14 | 2-Dehydro-3-deoxyphosphogluconate aldolase |
| 4.1.3.1 | Isocitrate lyase |
| 4.1.3.2 | Malate synthase |
| 4.1.3.4 | Hydroxymethylglutaryl-CoA lyase |
| 4.1.3.5 | Hydroxymethylglutaryl-CoA synthase |
| 4.1.3.7 | Citrate (si)-synthase |
| 4.1.3.8 | ATP citrate (pro-S)-lyase |
| 4.1.3.16 | 4-Hydroxy-2-oxoglutarate aldolase |
| 4.1.3.18 | Acetolactate synthase |
| 4.1.3.20 | N-Acylneuraminate-9-phosphate synthase |
| 4.1.3.21 | Homocitrate synthase |
| 4.1.3.22 | Citramalate lyase |
| 4.1.3.27 | Anthranilate synthase |
| 4.1.99.1 | Tryptophanase |
| 4.2.1.2 | Fumarate hydratase |
| 4.2.1.3 | Aconitate hydratase |
| 4.2.1.4 | Citrate dehydratase |
| 4.2.1.9 | Dihydroxy-acid dehydratase |
| 4.2.1.10 | 3-Dehydroxyquinate dehydratase |
| 4.2.1.11 | Phosphopyruvate hydratase (enolase) |
| 4.2.1.13 | l-Serine dehydratase |

TABLE 1-continued

| EC Number | Chemical Name |
|---|---|
| 4.2.1.16 | Threonine dehydratase |
| 4.2.1.17 | Enoyl-CoA hydratase |
| 4.2.1.18 | Methylglutaconyl-CoA hydratase |
| 4.2.1.19 | Imidazoleglycerol-phosphate dehydratase |
| 4.2.1.20 | Tryptophan synthase |
| 4.2.1.22 | Cystathionine B-synthase |
| 4.2.1.24 | Porphobilinogen synthase |
| 4.2.1.33 | 3-Isopropylmalate dehydratase |
| 4.2 1.46 | dTDPglucose 4,6-dehydratase |
| 4.2.1.47 | GDPmannose 4,6-dehydratase |
| 4.2.1.49 | Urocanate hydratase |
| 4.2.1.51 | Prephenate dehydratase |
| 4.2.1.52 | Dihydrodipicolinate synthase |
| 4.2.1.55 | 3-Hydroxybutyryl-CoA dehydratase |
| 4.2.1.58 | Crotonoyl-[acyl-carrier-protein] hydratase |
| 4.2.1.59 | 3-Hydroxyoctanoyl-[acyl-carrier protein] dehydratase |
| 4.2.1.60 | 3-Hydroxydecanoyl-[acyl-carrier protein] dehydratase |
| 4.2.1.61 | 3-Hydroxypalmitoyl-[acyl-carrier protein]dehydratase |
| 4.2.1.75 | Uroporphyrinogen-III synthase |
| 4.2.1.80 | 2-Oxopent-4-enoate hydratase |
| 4.2.99.2 | Threonine synthase |
| 4.2.99.8 | Cysteine synthase |
| 4.2.99.9 | O-Succinylhomoserine (thiol)-lyase |
| 4.3.1.1 | Aspartate ammonia-lyase |
| 4.3.1.2 | Methylaspartate ammonia-lyase |
| 4.3.1.3 | Histidine ammonia-lyase |
| 4.3.1.5 | Phenylalanine ammonia-lyase |
| 4.3.2.1 | Argininosuccinate lyase |
| 4.3.2.2 | Adenylosuccinate lyase |
| 4.4.1.1 | Cystathionine g-lyase |
| 4.4.1.8 | Cystathionine β-lyase |
| 4.4.1.15 | D-Cysteine desulfhydrase |
| 4.6.1.1 | Adenylate cyclase |
| 4.6.1.3 | 3-Dehydroquinate synthase |
| 4.6.1.4 | Chorismate synthase |
| 4.99.1.1 | Ferrochelatase |
| ISOMERASES | |
| 5.1.3.1 | Ribulose-phosphate 3-epimerase |
| 5.1.3.2 | UDPglucose 4-epimerase |
| 5.1.3.4 | l-Ribulose-phosphate 4-epimerase |
| 5.1.3.6 | UDPglucuronate 4-epimerase |
| 5.1.3.7 | UDP-N-acetylglucosamine 4-epimerase |
| 5.1.3.12 | UDPglucuronate 54-epimerase |
| 5.1.3.13 | dTDP-4-Dehydrorhamnose 3,5-epimerase |
| 5.1.3.14 | UDP-N-acetylglucosamine 2-epimerase |
| 5.1.99.1 | Methylmalonyl-CoA epimerase |
| 5.2.1.2 | Maleylacetoacetate isomerase |
| 5.2.1.3 | Retinal isomerase |
| 5.2.1.7 | Retinol isomerase |
| 5.3.1.1 | Triose-phosphate isomerase |
| 5.3.1.3 | Arabinose isomerase |
| 5.3.1.4 | l-Arabinose isomerase |
| 5.3.1.5 | Xylose isomerase |
| 5.3.1.6 | Ribose-5-phosphate isomerase |
| 5.3.1.8 | Mannose-6-phosphate isomerase |
| 5.3.1.9 | Glucose-6-phosphate isomerase |
| 5.3.1.16 | N-(54-Phospho-d-ribosylformimino)-5-amino-1-(544-phosphoribosyl)-4-imidazolecarboxamide isomerase |
| 5.3.3.2 | Isopentenyl-diphosphate 3-isomerase |
| 5.3.99.3 | Prostaglandin-E synthase |
| 5.3.99.5 | Thromboxane-A synthase |
| 5.4.2.1 | Phosphoglycerate mutase |
| 5.4.2.2 | Phosphoglucomutase |
| 5.4.2.3 | Phosphoacetylglucosamine mutase |
| 5.4.2.8 | Phosphomannomutase |
| 5.4.3.8 | Glutamate-1-semialdehyde 2,1-aminomutase |
| 5.4.99.2 | Methylmalonyl-CoA mutase |
| 5.4.99.5 | Chorismate mutase |
| 5.4.99.7 | Lanosterol synthase |
| 5.5.1.4 | myo-Inositol-l-phosphate synthase |
| LIGASES | |
| 6.2.1.3 | Long-chain-fatty-acid-CoA ligase |
| 6.3.1.1 | Aspartate-ammonia ligase |
| 6.3.1.2 | Glutamate-ammonia ligase |
| 6.3.1.4 | Aspartate-ammonia ligase (ADP-forming) |
| 6.3.1.5 | NAD+ synthetase |

TABLE 1-continued

| EC Number | Chemical Name |
|---|---|
| 6.3.2.1 | Pantoate-β-alannine ligase |
| 6.3.2.2 | Glutamate-cysteine ligase |
| 6.3.2.3 | Glutathione synthase |
| 6.3.2.5 | Phosphopantothenate-cysteine ligase |
| 6.3.2.6 | Phosphoribosylaminoimidazole-succinocarboxamide synthase |
| 6.3.2.7 | UDP-N-Acetylmuramoyl-l-alanyl-d-glutamate-lysine ligase |
| 6.3.2.8 | UDP-N-acetylmuramate-alanine ligase |
| 6.3.2.9 | UDP-N-acetylmuramoylalanine-D-glutamate ligase |
| 6.3.2.10 | UDP-N-acetylmuramoylalanyl-D-glutamyl-lysine-D-alanyl-D-alanine ligase |
| 6.3.2.13 | UDP-N-acetylmuramoylalanyl-D-glutamate-2,6-diaminopimelate ligase |
| 6.3.3.1 | Phosphoribosylglycinamide cyclo-ligase |
| 6.3.4.1 | GMP synthase |
| 6.3.4.2 | CTP synthase |
| 6.3.4.3 | Formate-tetrahydrofolate ligase |
| 6.3.4.4 | Adenylosuccinate synthase |
| 6.3.4.5 | Argininosuccinate synthase |
| 6.3.4.7 | Ribose-5-phosphate-ammonia ligase |
| 6.3.4.13 | Phosphoribosylamine-glycine ligase |
| 6.3.4.16 | Carbamoyl-phosphate synthase (ammonia) |
| 6.3.4.17 | Formate-dihydrofolate ligase |
| 6.3.5.1 | NAD+ synthetase (glutamine-hydrolysing) |
| 6.3.5.2 | GMP synthetase (glutamine-hydrolysing) |
| 6.3.5.3 | Phosphoribosylformylglycinamidine synthetase |
| 6.3.5.4 | Asparagine synthase (glutamine-hydrolysing) |
| 6.3.5.5 | Carbamoyl-phosphate synthase (glutamine-hydrolysing) |
| 6.4.1.1 | Pyruvate carboxylase |
| 6.4.1.2 | Acetyl-CoA carboxylase |
| 6.4.1.3 | Propionyl-CoA carboxylase |
| 6.4.1.4 | Methylcrotonoyl-CoA carboxylase |
| DEHYDROGENASES | |
| 1.1.1.1 | Alcohol dehydrogenase |
| 1.1.1.3 | Homoserine dehydrogenase |
| 1.1.1.8 | Glycerol-3-phosphate dehydrogenase |
| 1.1.1.14 | l-Iditol dehydrogenase |
| 1.1.1.22 | UDPglucose dehydrogenase |
| 1.1.1.23 | Histidinol dehydrogenase |
| 1.1.1.25 | Shikimate dehydrogenase |
| 1.1.1.27 | Lactate dehydrogenase |
| 1.1.1.29 | Glycerate dehydrogenase |
| 1.1.1.30 | 3-Hydroxybutyrate dehydrogenase |
| 1.1.1.31 | 3-Hydroxyisobutyrate dehydrogenase |
| 1.1.1.35 | 3-Hydroxyacyl-CoA dehydrogenase |
| 1.1.1.37 | Malate dehydrogenase |
| 1.1.1.39 | Malate dehydrogenase (decarboxylating) |
| 1.1.1.41 | Isocitrate dehydrogenase (NAD+) |
| 1.1.1.44 | Phosphogluconate dehydrogenase (decarboxylating) |
| 1.1.1.45 | l-Gulonate dehydrogenase |
| 1.1.1.49 | Glucose-6-phosphate dehydrogenase |
| 1.1.1.56 | Ribitol dehydrogenase |
| 1.1.1.79 | Glyoxylate reductase (NADP+) |
| 1.1.1.82 | Malate dehydrogenase (NADP+) |
| 1.1.1.85 | 3-Isopropylmalate dehydrogenase |
| 1.1.1.95 | Phosphoglycerate dehydrogenase |
| 1.1.1.105 | Retinol dehydrogenase |
| 1.1.1.130 | 3-Dehydro-L-gulonate 2-dehydrogenase |
| 1.1.1.157 | 3-Hydroxybutyryl-CoA dehydrogenase |
| 1.1.1.158 | UDP-N-acetylmuramate dehydrogenase |
| 1.1.1.204 | Xanthine dehydrogenase |
| 1.1.1.205 | IMP-dehydrogenase |
| 1.1.99.1 | Choline dehydrogenase |
| 1.1.99.5 | Glycerol-3-phosphate dehydrogenase |
| 1.2.1.3 | Aldehyde dehydrogenase (NAD+) |
| 1.2.1.7 | Benzaldehyde dehydrogenase (NADP+) |
| 1.2.1.8 | Betaine-aldehyde dehydrogenase |
| 1.2.1.11 | Aspartate-semialdehyde dehydrogenase |
| 1.2.1.12 | Glyceraldehyde-3-phosphate dehydrogenase |
| 1.2.1.13 | Glyceraldehyde-3-phosphate dehydrogenase |
| 1.2.1.16 | Succinate-semialdehyde dehydrogenase (NAD(P)+) |
| 1.2.1.18 | Malonate semialdehyde dehydrogenase (acetylating) |
| 1.2.1.21 | Glycolaldehyde dehydrogenase |
| 1.2.1.23 | 2-Oxoaldehyde dehydrogenase (NAD+) |
| 1.2.1.24 | Succinate-semialdehyde dehydrogenase |
| 1.2.1.25 | 2-Oxoisovalerate dehydrogenase (acylating) |
| 1.2.1.27 | Methylmalonate-semialdehyde dehydrogenase (acylating) |

TABLE 1-continued

| EC Number | Chemical Name |
|---|---|
| 1.2.1.31 | l-Aminoadipate-semialdehyde dehydrogenase |
| 1.2.1.32 | Aminomuconate-semialdehyde dehydrogenase |
| 1.2.1.36 | Retinal dehydrogenase |
| 1.2.1.41 | Glutamate-5-semialdehyde dehydrogenase |
| 1.2.1.52 | Oxoglutarate dehydrogenase |
| 1.2.4.1 | Pyruvate dehydrogenase (lipoamide) |
| 1.2.4.2 | Oxoglutarate dehydrogenase (lipoamide) |
| 1.3.1.1 | Dihydrouracil dehydrogenase (NAD+) |
| 1.3.1.2 | Dihydropyrimidine dehydrogenase (NADP+) |
| 1.3.1.8 | Acyl-CoA dehydrogenase (NADP+) |
| 1.3.1.13 | Prephenate dehydrogenase (NADP+) |
| 1.3.5.1 | Succinate dehydrogenase (ubiquinone) |
| 1.3.99.1 | Succinate dehydrogenase |
| 1.3.99.2 | Butyryl-CoA dehydrogenase |
| 1.3.99.3 | Acyl-CoA dehydrogenase |
| 1.3.99.7 | Glutaryl-CoA dehydrogenase |
| 1.3.99.10 | Isovaleryl-CoA dehydrogenase |
| 1.4.1.1 | Alanine dehydrogenase |
| 1.4.1.2 | Glutamate dehydrogenase |
| 1.4.1.7 | Serine dehydrogenase |
| 1.4.1.8 | Valine dehydrogenase (NADP+) |
| 1.4.1.9 | Leucine dehydrogenase |
| 1.4.1.10 | Glycine dehydrogenase |
| 1.4.1.19 | Tryptophan dehydrogenase |
| 1.4.4.2 | Glycine dehydrogenase (decarboxylating) |
| 1.5.1.6 | Formyltetrahydrofolate dehydrogenase |
| 1.5.1.7 | Saccharopine dehydrogenase (NAD+, L-lysine-forming) |
| 1.5.1.8 | Saccharopine dehydrogenase (NADP+, L-lysine-forming) |
| 1.5.1.9 | Saccharopine dehydrogenase (NAD+, L-glutamate-forming) |
| 1.5.1.10 | Saccharopine dehydrogenase (NADP+, L-glutamate-forming) |
| 1.5.1.12 | 1-Pyrroline-5-carboxylate dehydrogenase |
| 1.5.99.1 | Sarcosine dehydrogenase |
| 1.5.99.2 | Dimethylglycine dehydrogenase |
| 1.5.99.8 | Proline dehydrogenase1 |
| 1.6.5.3 | NADH dehydrogenase (ubiquinone) |
| 1.8.1.3 | Hypotaurine dehydrogenase |
| 1.8.1.4 | Dihydrolipoamide dehydrogenase |
| 1.8.2.1 | Sulfite dehydrogenase |

The approach described in more detail below could be applied to various subclasses of oxidoreductase enzymes. For example, the interface used for oxidoreductases acting on NADH could readily be adapted to oxidoreductases acting on flavodoxin as donor by substituting $FADH_2$ for NADH when assembling the interface.

In certain embodiments of the invention, the bioelectronic interface is fabricated on a glassy carbon electrode (GCE) using a carbon-nitrogen bond, which is stable at both high potentials (−1100 mV to 1100 mV) and high temperatures (Adams, 1969, Woodward, 1985). However, other electrically conductive carbon electrodes may be used, including vitreous reticulated carbon electrodes.

One aspect of the present invention is a method comprising molecular self assembly that is utilized to fabricate renewable bioelectronic interfaces on GCEs. Glycine (Gly) and the polycation poly(ethyleneimine) (PEI) may be used to couple the electron mediator, cofactor, and enzyme to a GCE in such a way that mediated electron transfer is achieved. The enzyme and cofactor may be removed by either raising or lowering the pH of the solution. Lowering the pH would protonate surface-bound carboxylic acid groups and thereby disrupt the electrostatic interactions between these groups and positively charged amine groups on the cofactor- and enzyme-modified PEI. After returning the pH to a value above the acid group's pK, PEI containing fresh cofactor and enzyme may then be reattached to regenerate bioelectronic activity. Raising the pH would deprotonate the positively charged amine groups on the cofactor- and enzyme-modified PEI and thereby disrupt the electrostatic interactions between these groups and surface-bound carboxylic acid groups. After returning the pH to a value below the amine group's pK, PEI containing fresh cofactor and enzyme may then be reattached to regenerate bioelectronic activity. Atomic force microscopy (AFM), chronoamperometry, constant potential amperometry, cyclic voltammetry, electrochemical impedance spectroscopy (EIS), and X-ray photoelectron spectroscopy (XPS) have been utilized to demonstrate the assembly process and the electrical activity of the resulting bioelectronic interface.

As another alternative, the carbon electrode may be treated, such as with a plasma, to ionize the surface and allow electrostatic bonding of a polyelectrolyte linker directly to the treated surface of the electrode.

Materials and Methods

Media and Strains

Mannitol dehydrogenase from *Thermotoga maritima* (TmMtDH) was expressed in *E. coli* BL21(DE3) (Tm-MtDH) and purified as previously described (Song et al., 2008).

Chemicals

Glycine (Gly), n-hydroxysuccinimide (NHS), 1-ethyl-3-(3-dimethylaminopropyl) carbodiimide (EDC), toluidine blue O (TBO), 3-carboxyphenyl boronic acid (CBA), β-nicotinamide adenine dinucleotide (NADH), PEI, glutaric dialdehyde (25% in water), D-fructose, D-glucose, sorbose, and arbinose were purchased from Sigma-Aldrich (St. Louis, Mo.). Ultrapure water (18.2 MΩ) was supplied by a Barnstead Nanopure-UV four-stage purifier (Barnstead International, Dubuque, Iowa).

Interface Formation

The GCEs (3 mm diameter, CH Instruments, Austin, Tex.) were polished on microcloth pads using 0.05 μm alumina powder (CH Instruments) and rinsed thoroughly with distilled water in an ultrasonic bath for 10 minutes. The cleaned electrodes were treated in a 100 mM phosphate buffer solution (PBS) (pH 7.4) containing 100 mM Gly by 14 cycles of cyclic voltammetry between 2500 mV and −1500 mV at a scan rate (v) of 100 mV $s^{-1}$ and then washed with ethanol and double distilled water to remove physically adsorbed material. After immobilization, the electrodes were washed with ethanol and water to remove the remaining unbound Gly. After drying in air, a blue thin film could be seen at the electrode surface. The thickness of the film could be controlled by the number of scans and the concentration of Gly.

The GCEs were incubated for 1 h in 0.1 mM TBO in 100 mM PBS (pH 7.4) in the presence of 2 mM NHS and 2 mM EDC, resulting in formation of an amide linkage between the amine group of the TBO and the carboxylic acid group of the Gly (Gly-TBO). The Gly-TBO-modified electrodes were soaked in a 10 mM aqueous solution of PEI containing 100 mM NaCl (pH 7.0) to form a Gly-TBO-PEI-modified interface. A 5 mM aqueous CBA solution was activated at room temperature in the presence of 2 mM NHS and 2 mM EDC in 100 mM PBS (pH 7.4) for 2 h. The NHS-modified CBA was then reacted with the Gly-TBO-PEI-functionalized electrodes at room temperature for 1 h, resulting in an amide linkage between the carboxylic acid group of the CBA and the amine group of the PEI. The resulting Gly-TBO-PEI-CBA-modified electrodes were reacted with a 1 mM solution of NADH in 100 mM PBS (pH 7.4) for 1 h and washed with water. The Gly-TBO-PEI-NADH-functionalized GCE were reacted with a 4.4 mg $mL^{-1}$ solution of TmMtDH in 100 mM PBS (pH 7.4) for 1 h at room temperature and cross-linked with 25% (v/v) glutaric dialdehyde in water for 20 min. The resulting TmMtDH-modified electrodes were used fro either the biocatalytic reduction of fructose or oxidation of mannitol.

The cofactor and enzyme-functionalized PEI layer was removed by incubating the electrode in 10 mM HCl (pH 2.0) at room temperature for 30 min. At pH values below the pKa of Gly (pKa~4.3), the carboxylic acid groups are protonated, thus decreasing electrostatic attraction between these groups and amine groups of PEI and allowing the TmMtDH-modified PEI to disengage from the surface. To reconstitute the interface, PEI, CBA, NADH, and TmMtDH were deposited onto the TBO-modified Gly monolayer using the protocol described above.

Surface Characterization
Atomic Force Microscopy

The bioelectronic interface's topography and surface roughness were measured using a Nanoscope IV multimode atomic force microscope (AFM) (Digital Instruments, Santa Barbara, Calif.) equipped with a "J" (100 μm) scanner. Silicon cantilevers (model NSC15/ALBS, resonance frequency 300 kHz, force constant 40 N m$^{-1}$, MicroMasch, Wilsonville, Oreg., USA) were used in tapping-mode at ambient temperature. Atomic force micrographs were acquired at scan rates ranging from 0.5 to 1 Hz at a scan angle of 0°. The height data were flattened using a second order fit. Features were obtained from cross-sectional analysis of the AFM data.

Ellipsometry

Ellipsometric thickness measurements on amine-terminated silicon wafers were made using a rotating analyzer ellipsometer (model M-44, J. A. Woollam) and WVASE32 software (included with the instrument). For layer-by-layer monitoring of growth, films were dried with N$_2$ after deposition of each layer, but in all other cases films were dried only after deposition of the entire film. A film refractive index of 1.5 was assumed in all thickness determinations.

X-ray Photoelectron Spectroscopy

To verify that electrooxidation can immobilize Gly on the surface of the electrode, the Gly-modified GCE surface was characterized by XPS (Ma et al., 2005). XPS data were acquired using a Perkin-Elmer Physical Electronics PHI 5400 X-ray photoelectron spectrometer equipped with a Mg X-ray source operated at 300 W (15 kV, 20 mA). The elemental nitrogen-to-carbon (N/C) ratio was calculated by dividing the total number of counts under the N(1s) band by that under the C(1s) (284.6 eV) band and multiplying the results by 100, after accounting for differences in atomic sensitivity factors for each element.

Electrochemical Characterization

A conventional three-electrode cell consisting of the enzyme-modified gold working electrode, a platinum auxiliary electrode, and a silver/silver chloride (Ag/AgCl) reference electrode was used for electrochemical measurements. Electrochemical impedance spectroscopy, chronoamperometry, constant potential amperometry, and cyclic voltammetry were performed using an electrochemical analyzer (CH1660B, CH Instruments) connected to a personal computer.

Chronoamperometry

Chronoamperometric experiments were conducted by stepping the potential of the working electrode from 200 mV to −400 mV, triggering the reduction of fructose in the vicinity of the electrode. The redox reactions that occur simultaneously at the Gly-TBO-PEI-NADH TmMtDH-modified electrode are summarized below:

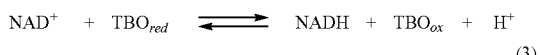

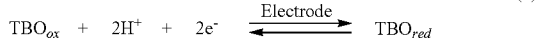

Origin (Version 7.6, OriginLab, Northampton, Mass.) was used to fit kinetic models to the resulting current vs. time data. Redox components with multiple binding modes exhibit a rate constant for each binding mode. Since NADH has two cis-diol moieties capable of forming a boronic acid linkage during interface formation, a biexponential decay model (Eq. 4) was used to described the current (I) as a function of time (t) (Zayats et al., 2002)

$$I = k'_{et}Q' \exp(-k'_{et}t) + k''_{et}Q'' \exp(-k''_{et}t) + I_c \quad (4)$$

Where, $k'_{et}$ and $k''_{et}$ are the electron transfer rate constants for the two binding modes Q' and Q" are amounts of charge transferred for the two binding modes. The surface coverage (Γ) of active enzyme can be calculated using Eq. 5 (Zayats et al., 2002), and $I_c$ is the charging current:

$$\Gamma = \frac{Q}{nFA} \quad (5)$$

where F, A, and n are Faraday's constant, electrode area, and the number of electrons transferred in the reaction (n=2), respectively.

Cyclic Voltammetry

Cyclic voltammetric experiments were conducted by sweeping the potential of the working electrode between 200 mV and −600 mV at a scan rate of 100 mV s$^{-1}$, causing fructose in the vicinity of the electrode to be reduced to mannitol in the positive direction and mannitol to be oxidized to fructose in the reverse direction. All electrochemical measurements were made in 100 mM PBS (pH 6.0) at 60° C. using an electrode with a controlled surface area of 0.07 cm$^2$. The slope of the calibration plot, which depicts peak current vs. concentration, is a measure of the biosensor's sensitivity. The maximum turnover rate ($TR_{max}$), which corresponds to the number of fructose molecules reduced per TmMtDH molecule per second, was calculated using Eq. 6 (Eisenwiener and Schulz, 1969):

$$TR_{max} = \frac{I_{cat}^{sat} - I_o}{nFA\Gamma} \quad (6)$$

where the background current ($I_0$) and saturation current ($I_{cat}^{sat}$) are given by the y-intercept of the calibration curve and the plateau current at a given concentration, respectively.

Electrochemical Impedance Spectroscopy

Electrochemical impedance spectroscopy (EIS) was used to confirm sequential deposition of molecular layers composing the bioelectronic interface and to examine the electron transfer characteristics on the interface. Impedance measurements were performed using an electrochemical analyzer composed of a potentiostat/frequency response detector (CHI660B) connected to a personal computer. To follow interface assembly, EIS measurements were made in 100 mM PBS (pH 6.0) containing 10 mM Fe(CN)$_6^{-3}$, 10 mM Fe(CN)$_6^{-4}$, and 10 mM NaCl over six frequency decades (10$^4$ Hz to 10$^{-2}$ Hz) at the open circuit potential of the Fe(CN)$_6^{-3/-4}$ solution (221 mV). A modified Randles electrical equivalent circuit model (Brug et al., 1984) with a solution resistance (R$_S$), charge transfer resistance (R$_{CT}$), and constant phase element (CPE) was fit to data using commercial software (Z-view, Version 2.1b, Scribner Associates Inc., Southern Pines, N.C.). The data were displayed as a Nyquist plot [imaginary impedance (Z$_{im}$) vs. real impedance (Z$_{re}$)].

Several models have been developed to analyze the electrochemical impedance spectra of redox polymer films. These models have considered further complexities such as the interaction between redox sites (Armstrong et al., 1986); migration effects (Mathias and Haas, 1992); slow reaction with the soluble species (Bonazzola and Calvo, 1998, Lang and Inzelt, 1991); non-uniform film thickness (Mathias and Haas, 1993). However the extensions of the simple interfacial electron transfer and diffusion charge propagation model have been made at the expense of a less clear physical insight. A simple modified Randles equivalent circuit was employed that consisted of the ohmic electrolyte resistance (R$_S$) in series with the impedance given by the interfacial double layer capacitance (C$_{DL}$) in parallel to the Faradaic charge transfer resistance (R$_{CT}$) and a finite diffusion impedance (Z$_D$) element. In this model, Z$_D$ consists of the Warburg parameter (W-R), response time (W-T), and power exponent (W-P). Calvo and Tagliazucchi have developed a model for electrochemical impedance to study the self-assembly of redox polymer modified films; Z$_D$ is given by Eq. 7 (Tagliazucchi and Calvo, 2007):

$$Z_D(\omega) = -f(\eta) = \frac{1}{C_F\omega}\left(\frac{\omega}{\omega_{tr}}\right)^{1/2} j^{1/2} \coth\left(\left[\frac{\omega}{\omega_{tr}}\right]^{1/2} j^{1/2}\right) \quad (7)$$

where C$_F$ is the Faradaic capacitance, ω is the angular frequency, ω$_{tr}$ is the transition frequency, and f(η) is the potential dependence of the film and given by Eq. 8 (Tagliazucchi and Calvo, 2007):

$$f(\eta) = \frac{1}{4}\left[\exp\left(\frac{\eta F}{2RT}\right) + \exp\left(-\frac{\eta F}{2RT}\right)\right]^2 \quad (8)$$

where η, F, R, and T are the apparent overpotential (η=E–E$^0$) is defined with respect to the reference electrode outside the film (Calvo and Wolosiuk, 2002), Faraday's constant, the ideal-gas constant, and temperature, respectively. The apparent diffusion coefficient could be determined by (Deng et al., 2007, Tagliazucchi and Calvo, 2007):

$$D_{app} = \omega_{tr} d^2 \quad (9)$$

where D$_{app}$ is the apparent diffusion coefficient of charges in the film and d is the film thickness. It is possible to obtain quantitative information on the charge propagation that results from electron transport through the interface and movement of ions to compensate the electrical charges.

Results and Discussion

Gly Adsorption

FIG. 1 shows the anodic immobilization of Gly in PBS (pH 7.4) at a scan rate of 100 mV s$^{-1}$. An oxidation peak observed at 1300 mV in the anodic direction (FIG. 1) represents the one-electron oxidation of the amino group into its corresponding cation radical. The magnitude of this peak increased with each successive scan, which is consistent with the literature suggesting the cation radicals form carbon-nitrogen linkages at the glassy carbon surface. A reduction peak at −420 mV, increased with each successive scan. The increases in both the oxidation and reduction peaks suggest that an electroconductive film is formed on the electrode surface.

Figure 2:
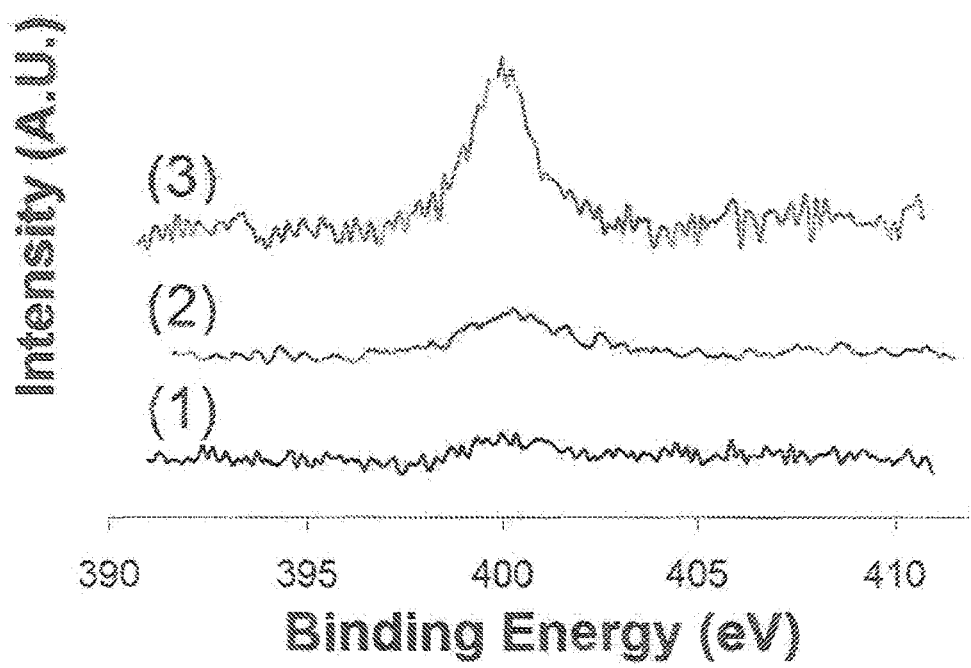
FIG. 2 is the N(1s) region of the XPS spectrum of the (1) bare GCE, (2) GCE after soaking in 100 mM Gly for 1 h, and (3) GCE after being electrooxidized by cyclic voltammetry between −1.5 and 2.5 V in a 50 mM Gly solution for 14 cycles.

The three curves in FIG. 2 show the XPS spectrum of the N1s region for the freshly polished GCE (Curve 1), GCE after soaking in 100 mM Gly for 1 h (Curve 2), and after redox cycling in a 100 mM Gly solution (Curve 3). A characteristic N1s peak appears at 399.4 eV, consistent with the formation of a carbon-nitrogen bond between an amine cation radical and an aromatic moiety of the GCE. To check that a strong, most likely covalent bond was established and that the glycine was not physically adsorbed on the surface, the electrode was immersed in 100 mM Gly for 60 min. at room temperature and sonicated in water for 10 min. The resulting XPS spectrum indicated only trace amounts of nitrogen on the electrode, presumably due to the physical adsorption of the Gly on the GCE. The nitrogen to carbon ratio (N/C) increased from 1.0 for the bare GCE to 1.8 for the electrode soaked in 100 mM Gly, and then to 4.1 for the electrode that experienced voltage cycling in the presence of Gly, according to the experimental procedure described above. These results suggest that voltage cycling resulted in a strong, most likely covalent C—N bond on the electrode.

Interface Assembly

Figure 3A:
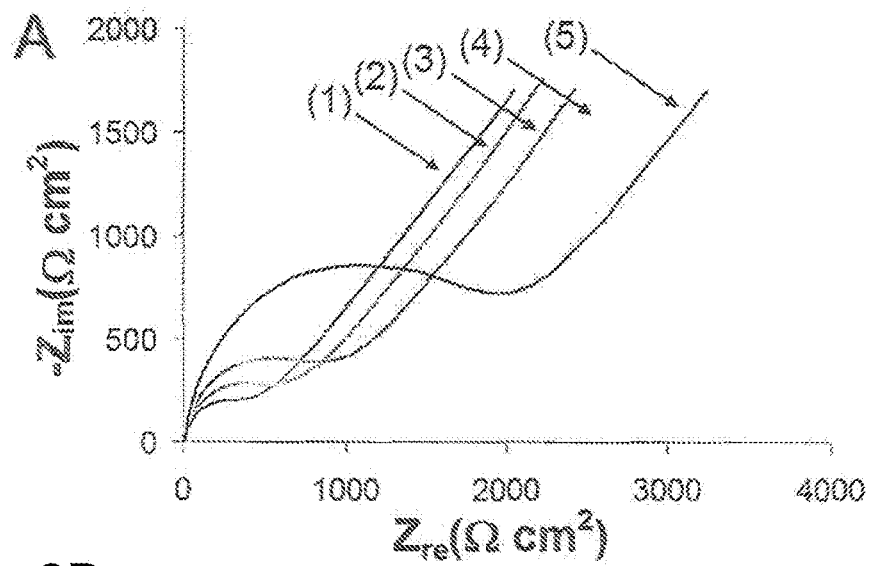
FIGS. 3A and 3B are Nyquist plots of (A): (1) Gly, (2) Gly-TBO, (3) Gly-TBO-PEI, (4) Gly-TBO-PEI-NADH, and (5) Gly-TBO-PEI-NADH-TmMtDH-modified electrode 100 mM PBS (pH 6.0) containing 10 mM Fe(CN)6$^{-3}$, 10 mM Fe(CN)6$^{-4}$, and 10 mM NaCl recorded at 221 mV and room temperature, and (B): (1) Gly-TBO-PEI-NADH-TmMtDH-modified electrode after washing with 10 mM HCl and the (2) Gly-TBO-PEI-NADH-TmMtDH-modified electrode after interface removal and reconstitution.
Figure 3B:
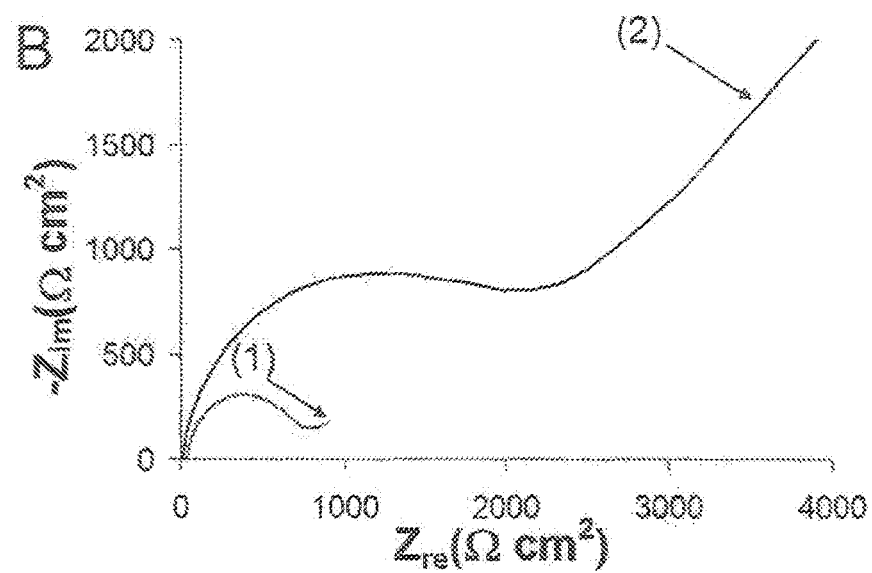

FIG. 3A shows the Faradaic impedance spectra of GCE modified with Gly, Gly-TBO, Gly-TBO-PEI, Gly-TBO-PEI-NADH, and Gly-TBO-PEI-NADH-TmMtDH (Curves 1-5, respectively). The charge transfer resistance increased with each subsequent layer, providing evidence of each step in the interface-formation process. FIG. 3(B) (Curve 1) shows the Nyquist plot for the Gly-TBO-PEI-NADH-TmMtDH-modified electrodes after being treated with 10 mM HCl. The R$_{CT}$ value after HCl treatment (780±0.9 Ωcm$^2$) was approximately equal to that for the original Gly-TBO-modified electrode (760±1.0 Ωcm$^2$), suggesting that the HCl treatment removed the NADH- and TmMtDH-modified PEI layers. After neutralizing pH and reabsorbing the PEI, CBA, NADH, and TmMtDH, the R$_{CT}$ increased to 2500±21 Ωcm$^2$ [FIG. 3(B), Curve 2], a value consistent with the original Gly-TBO-PEI-NADH-TmMtDH-modified electrode (2300±20 Ωcm$^2$). These data suggest that the NADH-TmMtDH-modified PEI was effectively removed by adjusting pH and then reconstituted.

The surface morphologies of the bare GCE, Gly-TBO-PEI-NADH-TmMtDH-modified electrode before HCl treatment, after HCl treatment, and after the readsorption of the Gly, TBO, PEI, NADH, and TmMtDH were characterized by AFM in order to investigate the homogeneity of the film. The root-mean-square (RMS) roughness of the Gly-TBO-PEI-NADH-TmMtDH-modified interface (3.26±0.28 nm) has a significantly different morphology compared to the bare GCE (0.88±0.62 nm). The increase in roughness suggests that the Gly, TBO, PEI, NADH, and TmMtDH are bound to the surface of the electrode. Following treatment with 10 mM HCl the RMS roughness decreases (1.26±0.27 nm) confirming that material is removed from the surface of the electrode. Upon readsorption of the PEI, NADH, and TmMtDH the RMS roughness increased to 3.51±0.92 nm. The measured RMS roughness is consistent with the adsorption of the original Gly-TBO-PEI-NADH-TmMtDH-interface, suggesting that the PEI, NADH, and TmMtDH were readsorbed onto the surface of the GCE. The average thickness of the Gly-TBO-PEI-NADH-TmMtDH was found to be 12.4±1.3 Å. The surface morphology and ellipsomemtric data are consistent with the EIS data, collectively providing strong evidence that that the Gly-TBO-PEI-NADH-TmMtDH-modified electrode can be successfully assembled, removed, and then reassembled on a GCE.

Interface Characterization

Enzyme Adsorption Kinetics

Figure 4A:
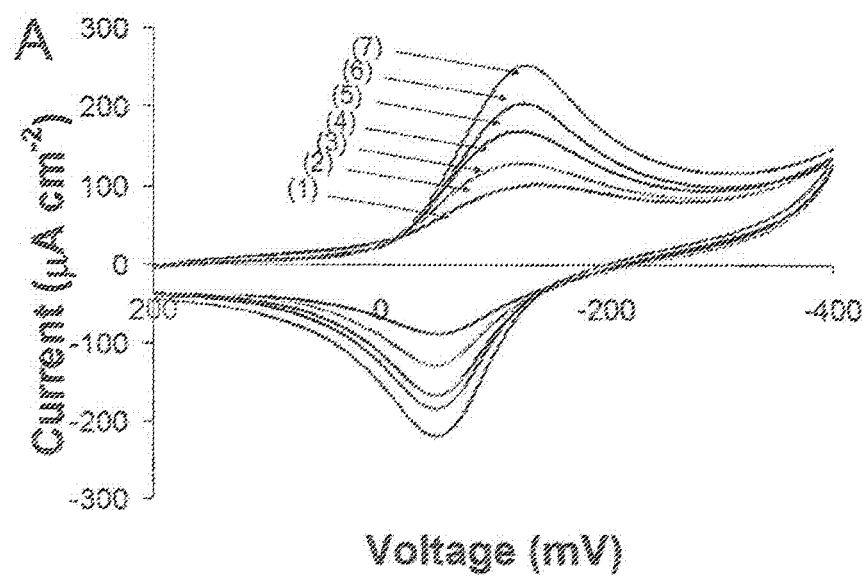
FIGS. 4A and 4B are (A) cyclic voltammograms of the Gly-TBO-PEI-NADH-functionalized electrode at various times of TmMtDH of reconstitution: (1) 0 min, (2) 6 min, (3) 15 min, (4) 30 min, (5) 60 min, (6) 120 min and (7) 240 min. (The data were recorded in 100 mM PBS (pH 6.0) containing 250 mM fructose at 60° C., and potential scan rate of 100 mV s$^{-1}$.), and (B) Peak electrocatalytic current at various time intervals, respectively.
Figure 4B:
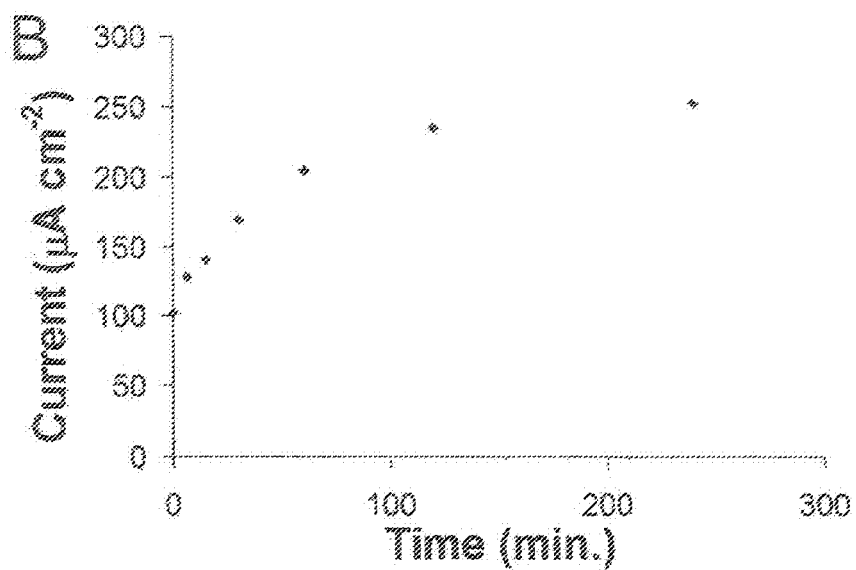

FIG. 4A shows cyclic voltammograms for the Gly-TBO-PEI-NADH-modified electrode in the presence of 250 mM fructose after different times of TmMtDH adsorption. FIG. 4B shows the peak anodic current at various adsorption times. A first-order kinetic model was fit to the peak-anodic-current vs time data, yielding a time constant of 58 min. This value is similar to that obtained for secondary alcohol dehydrogenase adsorption on a cysteine-TBO-NADP$^+$-modified interface assembled on a gold-coated silicon wafer (43 min).

Scan Rate Effects

Figure 5A:
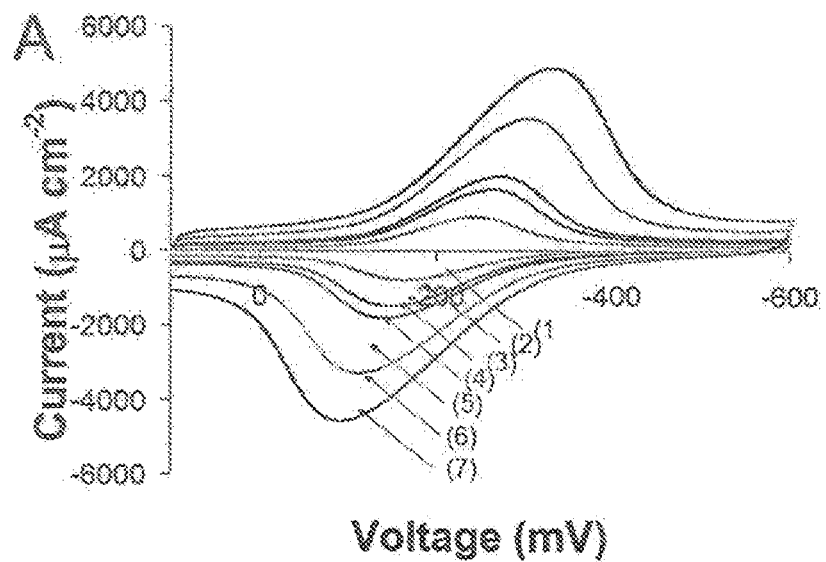
FIGS. 5A and 5B are (A) cyclic voltammograms of the Gly-TBO-PEI-NADH-TmMtDH-functionalized electrode in 100 mM PBS (pH 6.0) containing 250 mM fructose at 60° C., at various potential scan rates: (1) 40 mV s$^{-1}$ (2) 60 mV s$^{-1}$, (3) 80 mV s$^{-1}$, (4) 100 mV s$^{-1}$, (5) 150 mV s$^{-1}$ (6) 200 mV s$^{-1}$, and (7) 300 mV s$^{-1}$, and (B) Dependence of anodic and cathodic peak currents on scan rate, respectively, with the error bars in FIG. 5B indicating the mean±the standard deviation (n=3).
Figure 5B:
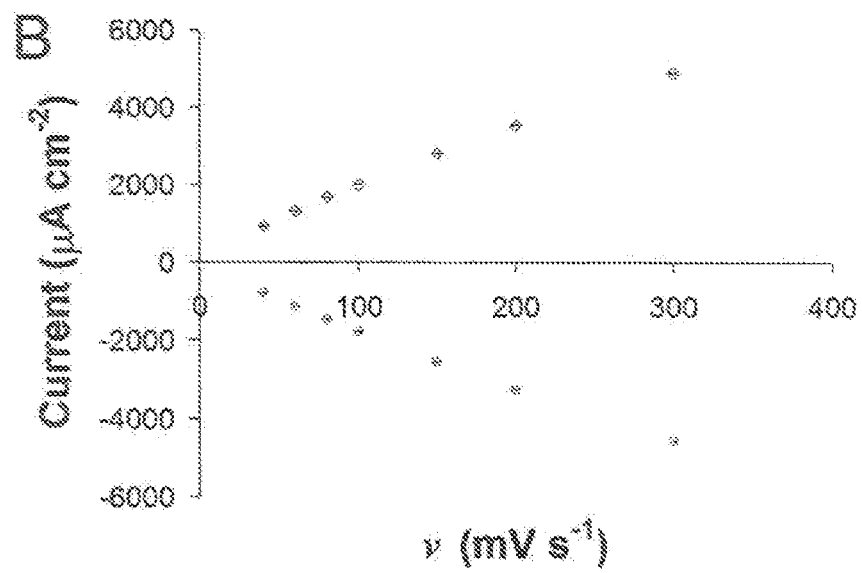

The charge transfer dynamics of the Gly-TBO-PEI-NADH-TmMtDH-modified electrode were studied by conducting cyclic voltammetry at scan rates ranging between 25 and 300 mV s$^{-1}$ in 100 mM PBS (pH 6.0) at 60° C. containing 250 mM fructose [FIG. 5A]. Both the anodic and cathodic peak currents increased linearly with scan rate [FIG. 5B], indicating that the redox reaction at the film electrode was a surface controlled process. Curves 1 through 7 are for increasing scan rates.

pH Effects

Figure 6:
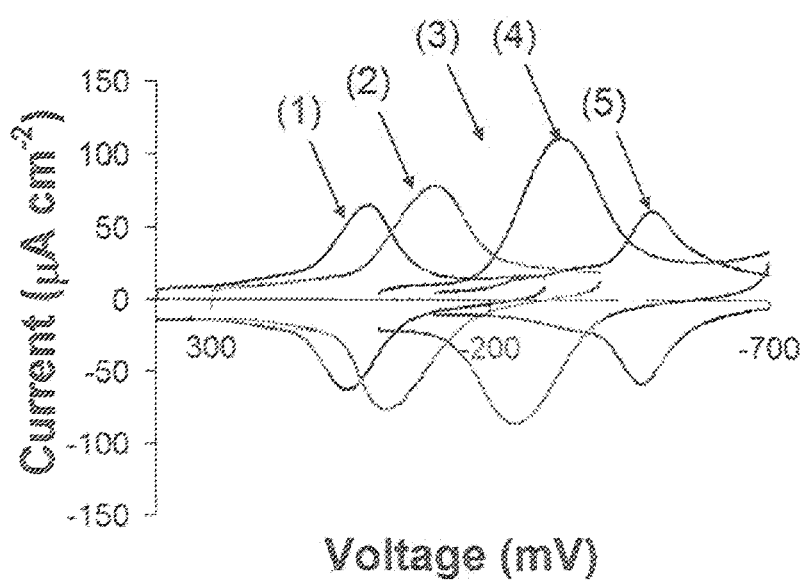
FIG. 6 is a cyclic voltammograms of the Gly-TBO-PEI-NADH-TmMtDH-functionalized electrode in 100 mM PBS containing 250 mM fructose at 60° C., at various pHs: (1) 2.0, (2) 4.0, (3) 6.0, (4) 8.0, and (5) 10.0.

The influence of pH on the redox reactions is shown in FIG. 6 for pH values of 2 (Curve 1), 4 (Curve 2), 6 (Curve 3), 8 (Curve 4) and 10 (Curve 5). The peak cathodic potential ($E_{PC}$) and peak anodic potentials ($E_{PA}$) varied linearly with pH, giving slopes of 63.0 mV (pH unit)$^{-1}$ for $E_{PC}$ and 65.0 mV (pH unit)$^{-1}$ for $E_{PA}$. According to the Nernst equation, the theoretical value of this slope should be 59.16 m/n mV (pH unit)$^{-1}$, where m and n correspond to the number of protons and electrons transferred during oxidation, respectively. The closeness of this value to the experimentally obtained slopes suggests that an equal number of electrons and protons are exchanged during the anodic and cathodic sweeps, respectively.

Apparent Diffusion Coefficient

Figure 7:
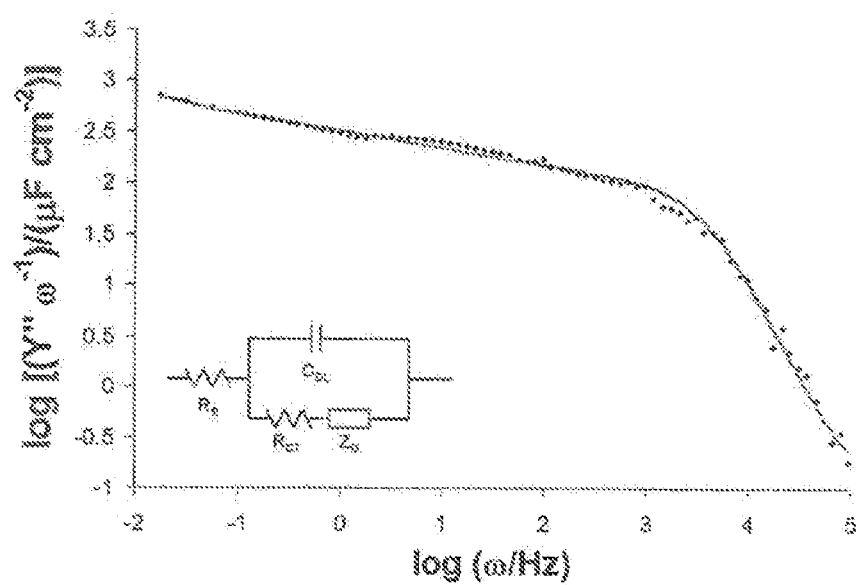
FIG. 7 is a plot of Log (Y"/ω) vs log (ω) plots for the Gly-TBO-PEI-NADH-TmMtDH-functionalized GCE in 100 mM PBS (pH 6.0), E=−200 mV. Solid line represents the best fit of the circuit. Inset: Equivalent circuit employed in study of the impedance spectra.

FIG. 7 shows the frequency dependence of the impedance for the Gly-TBO-PEI-NADH-TmMtDH-modified GCE. At formal potential, the Gly-TBO-PEI-NADH-TmMtDH-modified GCE displayed two distinct regions, as predicted by the finite line model of Albrey (Albery et al., 1990). This behavior is consistent with those of other redox polymer systems (Musiani, 1990). Fitting the spectrum to the equivalent circuit in the lower inset of FIG. 7, yielded best fit values for $R_S$, $C_{DL}$, W-R, W-T and W-P of 137±17.0Ω, 8.79±0.96×10$^{-8}$ F, 6.8±4.8×10$^4$Ω, 48.6±0.75 s and 0.86±0.05, respectively. The transition frequency was determined to be 4.6±0.7×10$^3$ Hz. The charge diffusion coefficient through the Gly-TBO-PEI-NADH-TmMtDH-modified GCE was 1.03±0.26×10$^{-10}$ cm$^2$ s$^{-1}$. The $D_{app}$ value is comparable to other supermolecular architectures in which a conductive polymer is used for mediated electron transfer (Ochmanska and Pickup, 1991, Pickup et al., 1984). Polymer layers are known to swell when placed in an electrolyte solution (Itano et al., 2005), suggesting the actual $D_{app}$ value might be slightly larger than that estimated above.

The calculated $D_{app}$ value should be considered a binary diffusion coefficient since both the $TBO_{OX}/TBO_{RED}$ centers could be responsible for the charge transfer inside the film, via electron hopping and counter ion diffusion (Tagliazucchi and Calvo, 2007). When the diffusion is ion-limited the high frequency resistance ($R_\infty$) becomes infinite at potentials far from the oxidation potential of the redox species (Mathias and Haas, 1993). However, if the diffusion is limited by electron hoping, $R_\infty$ is independent of the applied potential (Tagliazucchi and Calvo, 2007). For the Gly-TBO-PEI-NADH-TmMtDH-modified electrode, $R_\infty$, measured at 10 kHz varies about 10 Ωcm$^2$ in the potential range −300 mV to 0 mV, indicating that the ion transport is fast therefore $D_{app}$ is the apparent diffusion coefficient for electron hoping.

Surface Properties

Figure 8:
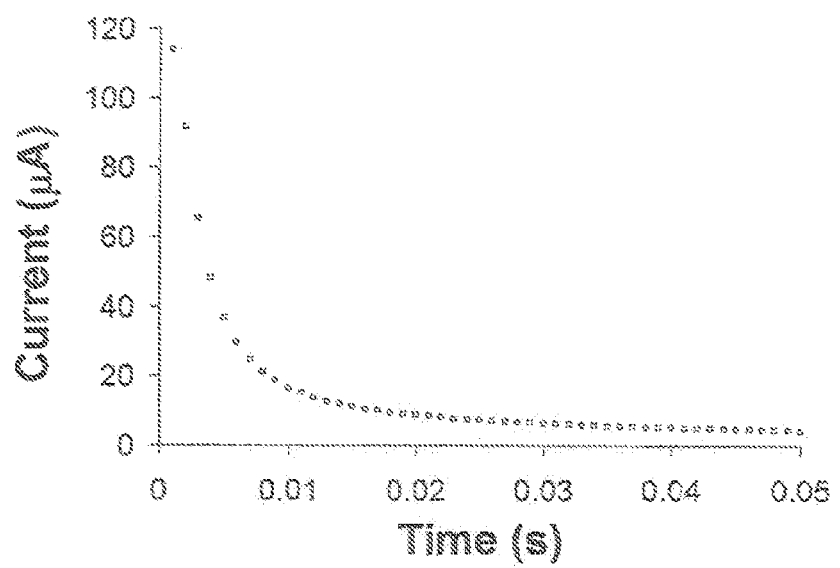
FIG. 8 is a chronoamperometric current transient following a potential step from Einitial=100 mV to Enna=−600 mV in 100 mM PBS (pH 6.0) containing 250 mM fructose at 60° C. for the Gly-TBO-PEI-NADHT mMtDH-functionalized electrode.

FIG. 8 shows the chronoamperometric current response for the Gly-TBO-PEI-NADH-TmMtDH-modified electrode following a step change in potential from 100 to −600 mV measured in 100 mM PBS (pH 6.0) at containing 250 mM fructose at 60° C. Fitting Eq. 4 to the chronoamperometric data gave k'$_{et}$ and k''$_{et}$ values of 281.3±1.5 and 103.7±1.9 s$^{-1}$ suggesting that the NADH binds to phenylboronic acid through both of the possible ligation modes. The differences in electron transfer coefficient indicating that one of the two CBA-NADH-TmMtDH-complexes transfers electrons about twice as fast the other. The Γ values for bioelectronic complexes possessing the two ligation modes were determined to be 1.1±0.2×10$^{-11}$ and 1.0±0.1×10$^{-11}$ mol cm$^{-2}$ using Eq. 5.

Figure 9A:
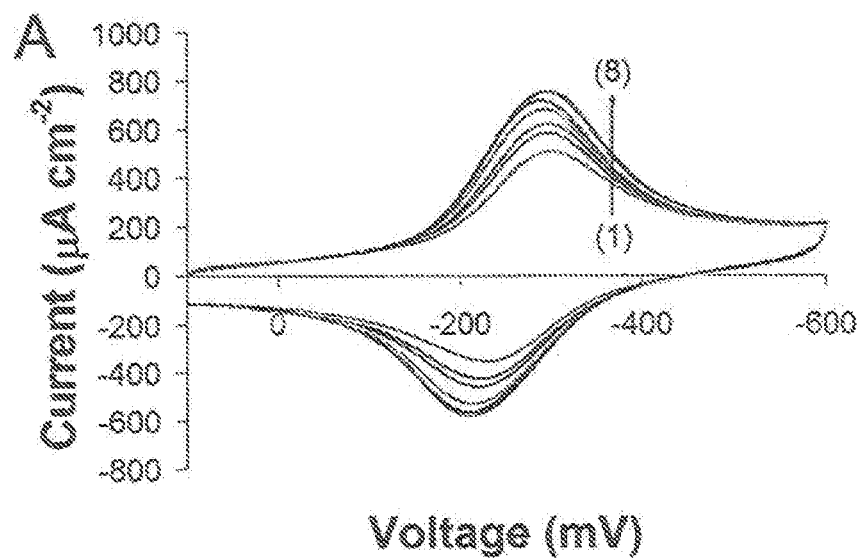
FIGS. 9A and 9B are (A) cyclic voltammograms of the Gly-TBO-PEI-NADH-TmMtDH-functionalized electrode in the presence of different concentrations of fructose in 100 mM PBS (pH 6.0) at 60° C.: (1) 0 mM, (2) 50 mM, (3) 100 mM, (4) 150 mM, (5) 200 mM, (6) 250 mM, (7) 300 mM, and (8) 350 mM, with the data recorded at a potential scan rate of 100 mV s$^{-1}$, and (B) peak electrocatalytic current at various fructose concentrations, respectively, with the error bars in FIG. 9B indicating the mean±the standard deviation (n=3).
Figure 9B:
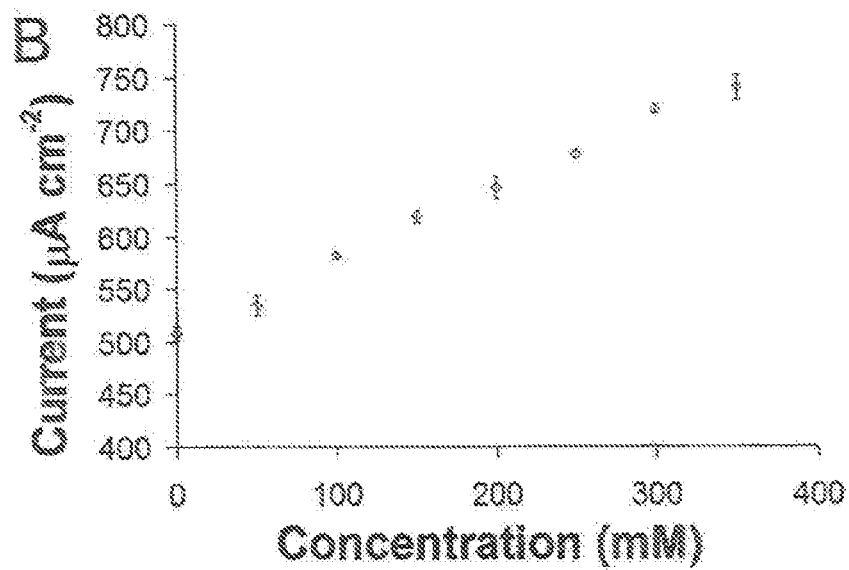

FIG. 9(A) shows the cyclic voltammograms of the Gly-TBO-PEI-NADH-TmMtDH-modified electrode at various fructose concentrations in 100 mM PBS (pH 6.0) at 60° C. The peak current varied linearly with fructose concentration [FIG. 9(B)] demonstrating that the interface could be used as a fructose biosensor. The slope of the calibration curve (0.70±0.01 µA) mM$^{-1}$ cm$^{-2}$) is a measure of the biosensor's sensitivity. At higher concentrations, the anodic current reached a saturation value ($I_{cat}^{sat}$=740.9±11.6 µA cm$^{-2}$). This value was used to calculate a TR$_{max}$, which represents the number of molecules of fructose reduction per TmMtDH molecule per second, of 57.5±2.8 s$^{-1}$, using Eq. 6 (Eisenwiener and Schulz, 1969). The Gly-TBO-PEI-NADH-TmMtDH-modified electrode exhibited 10% loss in activity upon operation for 24 h at 60° C. Following storage at room temperature in 100 mM borate buffer (pH 7.0) the Gly-TBO-PEI-NADH-TmMtDH-modified interface exhibited a 50% activity loss after 14 days.

The selectivity of the Gly-TBO-PEI-NADH-TmMtDH-modified electrode was examined by testing alternative substrates. Table 2 shows the sensitivity and turnover rate of the Gly-TBO-PEI-NADH-TmMtDH-modified electrode to fructose, glucose, arbinose, and sorbose. These data are consistent with the literature values for TmMtDH, indicating that the electrode has little activity for sugars besides fructose (Song et al., 2008).

TABLE 2

| Compound | $I_{cat}^{sat}$ (µA cm$^{-2}$) | Sensitivity (µA mM$^{-1}$ cm$^{-2}$) |
|---|---|---|
| Fructose | 748.2 ± 11.7 | 10.1 ± 0.2 |
| Glucose | 530.7 ± 2.2 | 0.2 ± 0.0 |
| Sorbose | 562.4 ± 1.4 | 0.4 ± 0.0 |
| Arbinose | 542.8 ± 9.1 | 0.3 ± 0.0 |

To confirm reviewability of the interface, the performance properties of the Gly-TBO-PEI-NADH-TmMtDH-modified electrode were measured before and after interface removal by HCl wash and reconstitution of the PEI, NADH, and TmMtDH. The values of Γ, k$_{et}$, $I_{cat}^{sat}$, sensitivity, and TR$_{max}$ for the reconstituted Gly-TBO-PEI-NADH-TmMtOHmodified electrode were virtually identical to those for the Gly-TBO-PEI-NADH-TmMtDH-modified electrode-modified electrode containing four cassettes before HCl treatment, suggesting that the interface could be removed and reconstituted without loss in performance.

The novel approach presented here uses functionalized polyelectrolytes to fabricate bioelectronic interfaces on GCEs that can be removed by a simple pH change and then reconstituted. The ability to reconstitute dehydrogenase-based bioelectronic interfaces without affecting performance can greatly reduce the operating costs of bioelectronic processes. The PEI, NADH, and TmMtDH can be removed by a decrease in pH and then reconstituted by passing PEI, NADH, and TmMtDH over the electrode. The Gly-TBO-PEI-NADH-TmMtDH-modified electrode has several potential applications including bioreactors and biofuel cells.

To assemble the bioelectronic interface, an electron mediator was first covalently bound to a GCE, followed by adsorption of a positively charged polyelectrolyte functionalized with its cofactor. Finally the enzymes were adsorbed by electrostatic interactions. AFM, chronoamperometry, cyclic voltammetry, EIS, and XPS were used to demonstrate sequential assembly of the layers and to characterize the performance of the resulting bioelectronic interfaces. The labile components of the interface could be removed by a decrease in pH and then reconstituted to regenerate the functional bioelectronic interface. The sensitivity, $I_{cat}^{sat}$, and $TR_{max}$ of the reconstituted interface ($0.7\pm0.1$ µA mM$^{-1}$ cm$^{-2}$, $734.2\pm16.9$ µA cm$^{-2}$, and $52.1\pm4.2$ s$^{1}$, respectively) were comparable to those of the original ($0.7\pm0.0$ µA mM$^{-1}$ cm$^{-2}$, $740.9\pm11.6$ µA cm$^{-2}$, and $57.5\pm2.8$ s$^{-1}$, respectively). The ability to develop a bioelectronic interface on a GCE has potential applications for biosensors and biocatalytic reactors (FIG. 1A), and biological fuel cells.

In accordance with certain embodiments of the invention, a bioelectronic interface containing exfoliated nanographite supports (e.g., exfoliated graphite nanoplatelets) modified with a polyelectrolyte may be employed to achieve increased enzymatic surface coverage (e.g., from about $2.1\times10^{-11}$ to about $3.3\times10^{-11}$ moles per square centimeter) as compared with known bioelectronic interfaces leading to improved sensitivity, saturation current, and turnover rate (e.g., about 5.5 µA mM$^{-1}$ cm$^{-2}$, about 185 µA cm$^{-2}$, and 24 s$^{-1}$, respectively). As an alternative, carbon nanotubes, fullerenes, and the like may be used rather than exfoliated graphite. The use of a polyelectrolyte allows the interface to be removed via a pH change to facilitate regeneration of a new interface on an electrically conductive carbon electrode. An example application this approach using is described below.

The incorporation of the exfoliated graphite, carbon nanotubes, and/or fullerenes into polyelectrolyte films is significant due to their unique chemical, physical, and electronic properties. The research group of Dr. Larry Drzal has developed a process to produce exfoliated graphite nanoplatelets (xGnP™) that range in thickness between 1 nm and 10 nm and diameter between 100 nm and 1000 nm. The chemical, physical, and electronic properties are consistent with carbon nanotubes and fullerenes. The cost of production ($5/pound) makes the xGnP a suitable replacement for carbon nanotubes and fullerenes. xGnP has recently been dispersed in sodium dodecylbenzene sulfonate (SDBS), sodium dodecyl sulfate (SDS), sulfated poly(styrene) (SPS), poly(acrylic acid) (PAA), poly(diallyldimethylammonium chloride) (PDAC) and polyethyleneimine (PEI). Coating xGnP with charged polymers increases both the stability of the suspension and the surface charge of the xGnP, making it possible to self assemble in layer-by-layer (LbL) films.

A novel assembly method which incorporates polyelectrolyte-modified xGnP into polyelectrolyte multilayers (PEMs) can be used for the fabrication of renewable bioelectronic interfaces. PEI was used to couple the xGnP, cofactor, and enzyme to a mediator-modified electrostatically functionalized electrically conductive carbon electrode in such a way that efficient electron transfer was achieved.

*Escherichia coli* (DH5αpADH B1M1-kan) culture containing a recombinant plasmid for secondary alcohol dehydrogenase (2° ADH) from *Thermoanaerobacter ethanolicus* was grown and purified in accordance with known techniques.

Tryptone, yeast extract, dithiothreitol, kanamycin, and ampicillin were obtained from Fisher Scientific (Pittsburgh, Pa.). All other chemicals, including cysteine, 1-ethyl-3-(3-dimethylaminopropyl) carbodiimide (EDC), n-hydroxysuccinimide (NHS), toluidine blue O (TBO), polyethyleneimine (PEI), 3-carboxy phenylboronic acid (CBA), β-nicotinamide adenine dinucleotide phosphate (NADP$^+$), glutaric dialdehyde (10% in water), 2-propanol, ethanol, 2-butanol, 2-pentanol, potassium ferrocyanide, and potassium ferricyanide were obtained from Sigma-Aldrich (St. Louis, Mo.). Ultrapure water (18.2 MΩ) was obtained from a Barnstead Nanopure-UV four-stage purifier (Barnstead International, Dubuque, Iowa).

A 0.1 g sample of xGnP was dispersed in a 1 g L$^{-1}$ aqueous PEI solution containing 0.1 M NaCl (pH 7.0). The graphite dispersion was tip-sonicated using a Branson B15 (Branson Ultrasonic Corporation, Danbury, Conn.) sonication immersion tip (100 W, pulsed) for 30 min followed by stirring for 24 h. The PEI coated xGnP were then filtered using a 0.22 □m Millipore filter (Millipore, Billerica, Mass.) and washed three times with deionized water, filtering after each washing step. The xGnP was then collected and redispersed in 100 mL DI water using mild tip sonication (50 W, pulsed) for 10 min.

Glassy carbon electrodes may be treated in a manner that imparts a charge on the surface, thereby facilitating binding of polyelectrolytes. In the embodiment described below, the GCE was immersed in cysteine, and the electrical potential of the GCE was cycled. This process is believed to oxidize cysteine's amino acid group, leading to a cationic nitrogen radical that forms a carbon-nitrogen bond on the surface of the GCE.

The cysteine-modified gold electrodes were incubated for 2 h in 100 µM TBO in a 0.1 M phosphate buffer solution (PBS) (pH 7.4) in presence of 2 mM NHS and 2 mM EDC, resulting in the formation of an amide linkage between TBO and the carboxyl group of the cysteine (MPA-TBO). The cysteine-TBO-modified electrodes were soaked in a 10 mM aqueous PEI/xGnP solution (pH 7.0) forming a cysteine-TBO-PEI/xGnP-modified interface. A 5 mM aqueous CBA solution was activated at room temperature in the presence of 2 mM NHS and 2 mM EDC in PBS (pH 7.4) for 2 h. The NHS-modified CBA was then reacted with the cysteine-TBO-PEI/xGnP-functionalized electrodes for 1 h at room temperature, resulting in an amide linkage between the CBA and the amine group of the PEI. The resulting cysteine-TBO-PEI/xGnP-CBA-modified electrodes was reacted with a 1 mM solution of NADP$^+$ in 0.1 M PBS (pH 7.4) for 1 h and then washed with water. The cysteine-TBO-PEI/xGnP-NADP$^+$-functionalized GCEs were reacted with a 4.4 mg mL$^{-1}$ solution of 2° ADH in 0.1 M PBS (pH 7.4) for 1 h at room temperature and cross-linked with 10% (v/v) glutaric dialdehyde in water for 20 min. The resulting 2° ADH-modified interfaces were used for the biocatalytic oxidation of 2-propanol.

The functionalized PEI-modified xGnP was removed by incubating the electrode in 0.01 M HCl (pH 2.0) for 30 min. Under these conditions, the carboxylic acid groups of the cysteine become protonated, thus decreasing the electrostatic interaction between the surface bound cysteine and the PEI. The decrease in electrostatic interaction allows the PEI to disengage from the surface. To reassemble the interface, PEI-modified xGnP, CBA, NADP$^+$, and 2° ADH can then be readsorbed using the protocol described above.

xGnPs may also be grafted onto a reticulated vitreous carbon (RVC) surface to increase surface area. One grafting method involves first assembling TBO molecules onto the carbon nanoparticles, followed by binding the TBO/carbon nanoparticle adduct on the RVC. This approach provides a high surface area, TBO/carbon composite electrode that reduces the NADH oxidation overpotential compared to bare carbon electrodes. In another approach, a Polyelectrolyte multilayer (PEM) base layer may be adsorbed directly onto the carbon, and other polyelectrolyte layer(s) functionalized with a mediator, cofactor, and enzyme may then be absorbed. A variety of carbon electrode substrate materials may be used, including GCE and RVC. The bioelectronic interface assembly methods would be substantially the same methods for each, although some optimization may be needed for each electrode material.

Figure 1A:
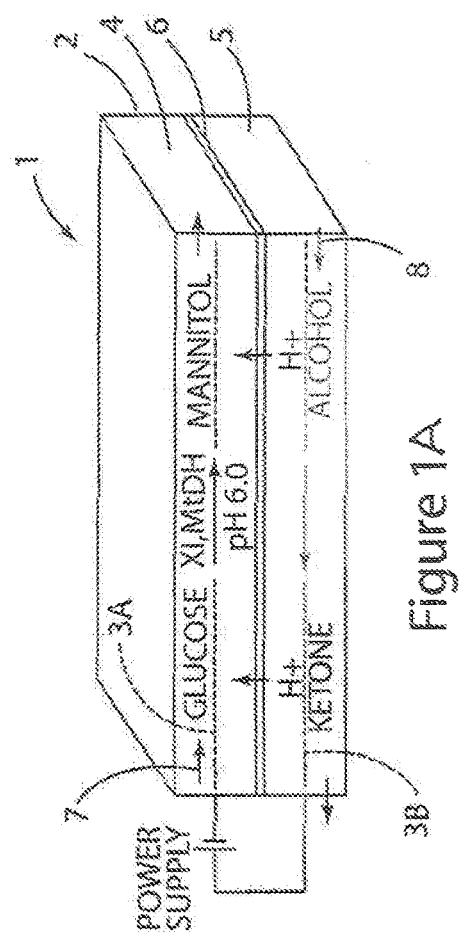
FIG. 1A is an electrobiocatalytic reactor.

In accordance with another embodiment of the invention, a renewable bioelectronic interface utilizing multiple nanostructured bioelectronic cassettes that are stacked in series to form bioelectronic interfaces having higher reaction capacities may also be utilized in the biocatalytic reactor 1 (FIG. 1A). The multilayered bioelectronic cassettes may be formed on carbon electrodes such as a GCE that may optionally include exfoliated graphite nanoplatelets or other carbon-based structures to increase the surface area, including carbon nanotubes, carbon black, graphite, and fullerenes. The techniques described in detail above to form an initial interface on a GCE substrate may be utilized to form an initial layer on various carbon substrates.

The polyanionic poly(acrylic acid) (PAA) and polycationic poly(ethyleneimine) (PEI) have been used for directed self-assembly of cassettes containing a mediator (toluidine blue O, [TBO]), a cofactor (NADP$^+$), and an enzyme (thermostable secondary alcohol dehydrogenase [2° ADH]) onto a carboxylic-acid-modified carbon electrode or electrostatically functionalized carbon electrode. However, a variety of other polyanionic and polycationic molecules may optionally be used instead to achieve mediated electron transfer within each cassette and across multiple cassettes in series.

In the multi-cassette embodiment described below, the secondary alcohol dehydrogenase (2° ADH) from *Thermoanaerobacter ethanolicus* was produced using recombinant *Escherichia coli* (DH5αpADH B1M1-kan) and then purified in accordance with known techniques.

1-ethyl-3-(3-dimethylaminopropyl) carbodiimide (EDC), n-hydroxysuccinimide (NHS), TBO, polyethyleneimine (PEI), poly(acrylic acid) (PAA), 3-carboxy phenylboronic acid (CBA), 3-nicotinamide adenine dinucleotide phosphate (NADP$^+$), glutaric dialdehyde (25% in water), 2-propanol, ethanol, 2-butanol, 2-pentanol, were obtained from Sigma-Aldrich (St. Louis, Mo.). Ultrapure water (18.2 MΩ) were obtained from a Barnstead Nanopure-UV four-stage purifier (Barnstead International, Dubuque, Iowa).

Electrically conductive carbon electrodes were treated with cysteine in a manner to covalently bind the cysteine to the carbon electrodes. This approach uses potential cycling to oxidize cysteine's amino group to a cationic radical, which forms a carbon-nitrogen bond with the carbon electrode. The cysteine-modified carbon electrodes were incubated tor 2 h in 0.1 mM TBO in a 100 mM phosphate buffer solution (PBS) (pH 7.4) in the presence of 2 mM NHS and 2 mM EDC, resulting in an amide linkage between the TBO and the cysteine. The cysteine-TBO-modified electrodes were immersed in a 10 mM aqueous PEI solution containing 100 mM NaCl (pH 7.0), forming a cysteine-TBO-PEI-modified interface. A 5 mM aqueous CBA solution was activated at room temperature in the presence of 5 mM NHS and 5 mM EDC in 100 mM PBS for 2 h. The NHS-modified CBA was then reacted with the cysteine-TBO-PEI-functionalized electrodes for 1 h at room temperature. The resulting cysteine-TBO-PEI-CBA-modified electrodes was immersed in a 1 mM solution of NADP$^+$ in 100 mM PBS for 1 h and then washed with water. To bind 2° ADH, the cysteine-TBO-PEI-NADP$^+$-functionalized carbon electrodes were immersed in a 4.4 mg mL$^{-1}$ solution of 2° ADH in 100 mM PBS for 1 h at room temperature. This step completes the fabrication of the first bioelectronic cassette, yielding a fully functional cysteine-TBO-PEI-NADP$^+$-2° ADH bioelectronic interface.

To add additional cassettes on top of the first, the 2° ADH-terminated interfaces were immersed in a 10 mM aqueous PEI solution containing 100 mM NaCl (pH 7.0), and washed with water to remove the residual PEI from the surface. The resulting PEI-modified electrodes were immersed in a 100 mM PAA solution (pH 5.5) and washed with water. The cysteine-TBO-PEI-NADP$^+$-2° ADH-PEI-PAA-modified electrodes were incubated for 2 h in 0.1 mM TBO in a 100 mM PBS in the presence of 2 mM NHS and 2 mM EDC, resulting in the formation of an amide linkage between the TBO and the PAA. The electrodes were then immersed in a 10 mM aqueous PEI solution (pH 7.0). The NHS-activated CBA was then reacted with cysteine-TBO-PEI-NADP$^+$-2° ADH-PEI-PAA-TBO-PEI-functionalized electrodes for 1 h at room temperature. The resulting CBA-modified electrodes were reacted with a 1 mM NADP$^+$ solution in 100 mM PBS for 1 h and then washed with water. The second cassette was completed by immersing the electrodes in a 4.4 mg mL$^{-1}$ 2° ADH solution in 100 mM PBS for 1 h at room temperature. The assembly process described above for the second cassette was carried out n times to add n PAA-TBO/PEI-NADP$^+$-2° ADH functional units on top of the first cassette, resulting in a total of n+1 bioelectronic cassettes in series. The resulting interface is described as a cysteine-TBO-PEI-NADP$^+$-2° ADH-[PAA-TBO/PEI-NADP$^+$-2° ADH]$_n$-modified interface.

The labile components of the interface were removed by incubating the electrode in 10 mM HCl (pH 2.0) for 30 min. At pH values below the pKa of MPA (pKa~4.3), the carboxylic acid group was protonated, thus decreasing the electrostatic interaction between the surface bound cysteine and the modified PEI and allowing the PEI to disengage from the surface. To reassemble the interface, the PEI, CBA, NADP$^+$, PAA, TBO, and 2° ADH were reattached onto the TBO-modified MPA monolayer using the protocol described above.

To optimize the performance properties of a bioreactor for each enzyme/reactant system, a variety of mediators, cofactors, and carbon electrode materials may be utilized. Furthermore, reactor geometry, liquid residence time, applied voltage, temperature, pH, etc. may adjusted to optimize performance for each system. A mathematical model that may be utilized in designing bioreactor 1 is described herein.

To optimize the performance of enzyme-based bioelectronic interfaces it is necessary to understand the relationship among the substrate/product transport, electron transport, and enzyme kinetics.

The mathematical models of those relationships result in highly non-linear differential equations. Both numerical solutions to the entire model and analytical solutions to simplified versions of the model have been developed for these problems.

A variety of numerical techniques including explicit finite difference (Jemmer, 1999) and Crank Nicholson (Bergel and Comtat, 1984) have been used to solve both transient and steady-state problems with a variety of different boundary conditions. Analytical solutions generally rely on the identification of suitable limiting cases is which the diffusion kinetic, and reaction equations can be linearized and solved. This approach has been used to analyze the kinetics of reaction at a polymer-modified electrode in which the species from solution reacts with a mediator bound within a film found at the electrode surface (Andrieux et al. 1982, Rahamathunissa and Rajendran, 2008, Scott and Bowden, 1994. Bartlett and Pratt developed numerical simulations to validate their analytical solutions to limiting cases of the model and to investigate the boundary regions between the different limiting cases (Bartlett and Pratt, 1995). However, these models have not been extended to enzyme systems with reversible kinetics.

We develop a model that extends the approach of Bartlett and Pratt to include bioelectronic interfaces having reversible enzymes, cofactors, and mediators. The model's predictions were verified with experimental results. The general approach developed takes into account reversible enzyme kinetics, mediator kinetics, substrate diffusion, product diffusion, and electron diffusion. To simplify the treatment, we exclude the effects of mass transport in solution outside the film. The model is restricted to steady state, and is limited to the case where the enzyme and electron mediator are bound within the film. The electrochemical behavior of the bioelectronic interface was characterized using chronoamperometry and compared with the model predictions. The analysts presented here could be used to design and optimize conditions for biofuel cell, biocatalysis, and biosensing applications.

Figure 10:
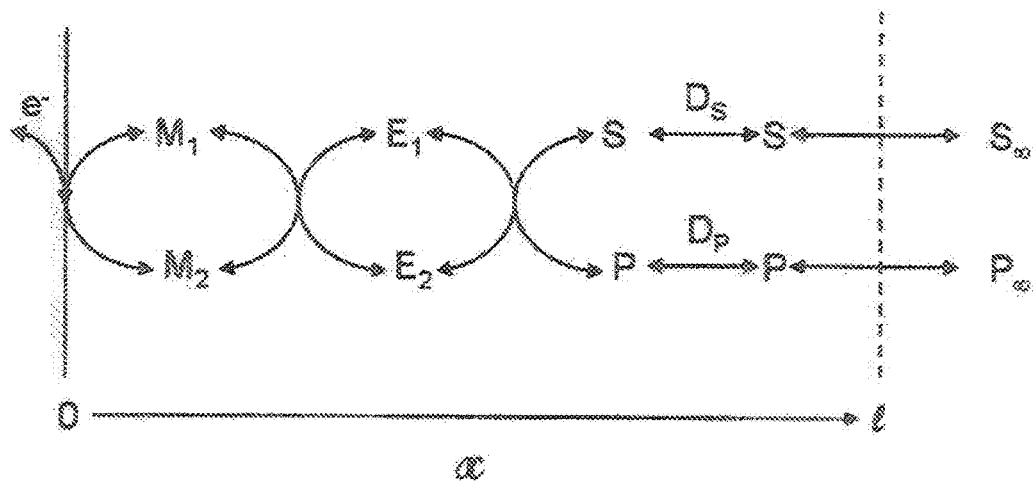
FIG. 10 is a schematic illustration of a typical enzyme membrane electrode showing the processes considered in a mathematical model for simulating and optimizing performance characteristics of an enzyme-based bioelectronics interface.

FIG. 10, shows the kinetic scheme for an enzyme-modified electrode (Bartlett and Pratt, 1995) based on a redox enzyme which follows an ordered bi-bi mechanism. In FIG. 10, S and P represent the substrate (reduced species) and product (oxidized species), respectively, $E_1$ and $E_2$ represent the reduced and oxidized forms of the enzyme/cofactor complex, respectively, and $M_1$ and $M_2$ represent the oxidized and reduced forms of the mediator, respectively. The enzyme is assumed to be immobilized in the film such that the concentration is uniform throughout the thickness (l) of the film. The substrate and the product are free to diffuse through the film with diffusion coefficients of $D_P$ and $D_S$, respectively. Partitioning of the substrate and product across the solution/membrane interface occurs, with partitioning coefficients of $K_S$ and $K_P$, respectively. We will only consider the situation where the mediator is covalently bound within the film and interacts with the enzyme reaction directly. Since the mediator is bound within the film the mediator diffusion coefficient ($D_M$) corresponds to the diffusion of charge through the matrix rather than the physical diffusion of the mediator.

The ordered bi-bi reaction of the enzyme with the substrate and cofactor is shown in Eq. (10):

(10)

where $k_1$ and $k_{-1}$ are the reaction rate constants describing the reaction of the enzyme (E) and the reduced cofactor ($C_1$) to form an enzyme/reduced cofactor complex ($EC_1$). $k_1$ and $k_2$ are the rate constants describing the reaction of $EC_1$ and substrate (S) to form the enzyme/cofactor/substrate ($EC_1S$). $k_3$ and $k_{-3}$ are the rate constants for the breakdown of $EC_1S$ into enzyme/oxidized cofactor complex ($EC_2$) and product (P). $k_4$ and $k_{-4}$ are the reaction rate constants describing the breakdown of $EC_2$ into E and the oxidized cofactor ($C_2$). $z_S$ and $z_B$ represent the stoichiometric coefficients of the substrate and the product, respectively, with respect to amount of the enzyme involved in the reaction, where the cofactor stoichiometry is assumed to be one. It is assumed that the enzyme and cofactor are directly bound within the film, indicating that the association and dissociation rate constants for $EC_1$ and $EC_2$ ($k_1$, $k_{-1}$, $k_4$, and $k_{-4}$) are negligible compared the rate constants for the enzyme reaction, suggesting Eq. (10) can be simplified to Eq. (11).

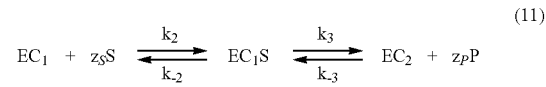

(11)

The other reaction within the film can be written as:

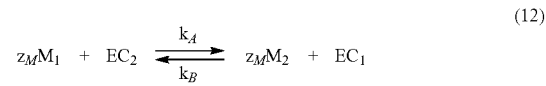

(12)

where $k_A$ and $k_B$ are the forward and reverse rate constants describing the reaction of the mediator ($M_1/M_2$) with $EC_1$ and $EC_2$. $z_M$ is the stoichiometric coefficient for the mediator with respect to the enzyme. The reaction at the electrode surface is give as Eq. (13).

$$M_2 \rightleftharpoons M_1 \quad (13)$$

The rate of this reaction is assumed to be to be fast relative to the enzyme reaction, so it is always in equilibrium. The rate of reaction with respect to product formation ($v_p$) can be written as:

$$vp = k_3[EC_1S] - k_{-3}[EC_2][P]^{z_p} \quad (14)$$

The reaction rates with respect to the substrate and mediator are related by stoichiometry which can be expressed as:

$$v_P = -\left(\frac{z_S}{z_P}\right)v_S = -\left(\frac{z_M}{z_P}\right)v_M \tag{15}$$

where $v_S$ and $v_M$ are the reaction rates with respect to the substrate and the electron mediator, respectively. For simplicity, here we assume that $z_S$, $z_P$, and $z_M$ are equal to 1. We can write the following partial differential equations describing diffusion and reaction within the film:

$$\frac{\partial [S]}{\partial t} = D_S \frac{\partial^2 [S]}{\partial x^2} - v_S \tag{16}$$

$$\frac{\partial [P]}{\partial t} = D_P \frac{\partial^2 [P]}{\partial x^2} - v_P \tag{17}$$

$$\frac{\partial [M_1]}{\partial t} = D_M \frac{\partial^2 [M_1]}{\partial x^2} - v_M \tag{18}$$

$$\frac{\partial [EC_1 S]}{\partial t} = k_2[S][EC_1] - k_{-2}[EC_1 S] - v_P \text{ and} \tag{19}$$

$$\frac{\partial [EC_2]}{\partial t} = v_P - k_A[M_1][EC_2] + k_3[M_2][EC_1] \tag{20}$$

It can be assumed that the enzyme is bound within the film and is not free to diffuse and assuming steady-state conditions, $\partial[EC_1 S]/\partial t = 0$. Introducing $[E_T]=[EC_1]+[EC_2]+[EC_1 S]$ and $[M_T]=[M_1]+[M_2]$ are the total concentration of immobilized enzyme and mediator, respectively.

$[EC_1 S]$ can be expressed as Eq. (21):

$$[EC_1 S] = \frac{k_2[S][E_T] + [EC_2](k_{-3}[P] - k_2[S])}{(k_{-2} + k_3 + k_2[S])} \tag{21}$$

Substituting Eq. (21) into Eq. (20) and solving for $[EC_2]$.

$$[EC_2] = \frac{k_3 k_b[M_2][E_T] + k_{-2} k_b[M_2][E_T] + k_2 k_3[S][E_T]}{[S](k_2 k_3 + k_2 k_a[M_1]) + [P](k_{-3} k_b[M_2] + k_{-2} k_{-3}) + k_2 k_{-3}[S][P] + (k_a[M_1] + k_b[M_2])(k_{-2} + k_3)} \tag{22}$$

Substituting Eqs. (21) and (22) into Eq. (14):

$$v_P = \frac{[E_T](k_2 k_3 k_a[M_1][S] - k_{-2} k_{-3} k_b[M_2][P])}{[S](k_2 k_3 + k_2 k_a[M_1]) + [P](k_{-3} k_b[M_2] + k_{-2} k_{-3}) + k_2 k_{-3}[S][P] + (k_a[M_1] + k_b[M_2])(k_{-2} + k_3)} \tag{23}$$

assuming steady state, Eqs. (16), (17), and (18) become:

$$D_S \frac{\partial^2 [S]}{\partial x^2} = v_S \tag{24}$$

$$D_P \frac{\partial^2 [P]}{\partial x^2} = v_P \tag{25}$$

$$D_M \frac{\partial^2 [M_1]}{\partial x^2} = v_M \tag{26}$$

Introducing the following dimensionless variables:

$$s = \frac{[S]}{K_S[S]_\infty} \tag{27}$$

$$p = \frac{[P]}{K_P[P]_\infty} \tag{28}$$

$$m = \frac{[M_1]}{[M_T]} \tag{29}$$

$$\chi = \frac{x}{l} \tag{30}$$

$$K = \frac{k_B}{k_A} \tag{31}$$

$$\mu = \frac{k_2 K_S[S]_\infty}{k_{-2} + k_3} \tag{32}$$

$$\lambda = \frac{k_{-3} K_P[P]_\infty}{k_{-2} + k_3} \tag{33}$$

$$\kappa^2 = \frac{k_A[E_T][M_T]l^2}{D_A K_P[P]_\infty} \tag{34}$$

$$\omega = \frac{k_3}{k_A[M_T]} \tag{35}$$

$$\rho = \frac{k_{-2}}{k_A[M_T]} \tag{36}$$

$$\alpha = \frac{D_A}{D_P} \tag{37}$$

$$\beta = \frac{D_A}{D_S} \tag{38}$$

$$A = \frac{z_M K_P[P]_\infty}{z_P[M_T]} \tag{39}$$

$$B = \frac{z_S K_P[P]_\infty}{z_P K_S[S]_\infty} \tag{40}$$

where s, p, and m are the dimensionless concentrations of the substrate, product, and mediator, respectively, normalized with respect to the total concentrations of substrate ($K_S[S]_\infty$), product ($K_P[P]_\infty$), and mediator ($[M_T]$) within the film, where subscript $\infty$ denotes the concentration in the bulk. The variables $K_S$ and $K_P$ represent the partition coefficients for the substrate and product, within the film. The normalized distance from the electrode is represented by $\chi$. K denotes the ratio of mediator reaction rates, $\mu$ and $\lambda$ represent the ratios of the substrate and product species concentration to the Michaelis-Menten constant for the substrate and product, respectively, $\kappa$ describes the balance between the diffusion within the film and its reaction with the enzyme, $\omega$ and $\rho$ denote the ratio of the forward and reverse enzyme reaction rate, respectively, $\alpha$ and $\beta$ are the ratios of substrate diffusion and product diffusivity, respectively, to mediator diffusivity. Finally, A is the stoichiometric ratio of substrate and mediator concentrations, and B is the stoichiometric ratio of product to mediator concentrations.

Substituting Eqs. (27) through (40) into Eq. (23) gives:

$$v_P = \frac{k^2 \alpha (s\mu\omega m - p\lambda\rho K(1-m))}{s\mu(\omega + m) + p(\lambda K(1-m) + p\lambda) + ps\mu\lambda(\omega + \rho) + m + K(1-m)} \tag{41}$$

Eqs. (24) through (26) become:

$$\frac{\partial^2 m}{\partial \chi^2} = \left(\frac{A}{\alpha}\right) v_P \quad (42)$$

$$\frac{\partial^2 s}{\partial \chi^2} = \left(\frac{B\beta}{\alpha}\right) v_P \quad (43)$$

$$\frac{\partial^2 p}{\partial \chi^2} = v_P \quad (44)$$

Eqs. (42) through (44) can be solved with the appropriate boundary conditions.

The substrate and the product are free to diffuse through the film with diffusion coefficients of $D_P$ and $D_S$, respectively. Partitioning of the substrate and product across the solution/membrane interface occurs, with partitioning coefficients of $K_S$ and $K_P$, respectively are given by Eqs. (45).

$$s|_{\chi=1} = p|_{\chi=1} = 1 \quad (45)$$

The diffusive flux of the product and substrate at the electrode/film interface is zero, leading to Eqs. (46).

$$\left.\frac{\partial s}{\partial \chi}\right|_{\chi=0} = \left.\frac{\partial p}{\partial \chi}\right|_{\chi=0} = 0 \quad (46)$$

Useful mechanistic information about the interaction of the substrate, product, and the mediator with the enzyme can be obtained by examining the potential dependence of the electrochemical reaction of the mediator at the electrode surface. We can assume that it remains in equilibrium and apply the Nernst equation:

$$E = E^0 + \frac{RT}{nF} \ln\frac{[M_1]_0}{[M_2]_0} \quad (47)$$

where $[M_1]_0$ and $[M_2]_0$ are the concentrations of the two forms of the mediator at the electrode surface. E and $E^0$ are the applied potential and the reversible potential for the bound mediator, respectively. R, T, n, and F are the gas constant temperature, electron stoichiometric coefficient, and Faraday's constant, respectively.

A dimensionless potential ($\varepsilon$) can be defined as:

$$\varepsilon = \frac{(E - E^0)nF}{RT} \quad (48)$$

Substituting Eq. (47) into Eq. (48) gives the boundary conditions for the dimensionless oxidized mediator concentration ($m_\varepsilon$) at the electrode surface.

$$m_\varepsilon = \frac{1}{1 + \exp(-\varepsilon)} \quad (49)$$

Since the mediator is bound within the film, the diffusion at the film/bulk interface is governed by the zero flux boundary condition.

$$\left.\frac{\partial m}{\partial \chi}\right|_{\chi=1} = 0 \quad (50)$$

The observed flux ($j_{obs}$) of [$M_2$] to the electrode, where it is converted to [$M_1$], can be measured at the electrode as current (I). The flux can also be modeled as mediator diffusion to the electrode, as expressed by Eq. (51).

$$j_{obs} = \frac{I}{nFA} = -D_A \left(\frac{d[M_1]}{dx}\right)_{x=0} \quad (51)$$

Since the mediator cannot escape from the film (dm/d$\chi$=0 at $\chi$=1) the rate of [S] reacting within the film is proportional to the flux of reduced mediator at the electrode's surface. Thus, the rate of [S] converted to [P] within the bioelectronic interface can be calculated from I.

The substrate and product participate in a reversible, equilibrium with an enzyme-substrate complex. A modified Michaelis-Menten kinetic model is most frequently used to describe the reversible behavior of the enzyme [Eq. (52)] (Segel, 1993).

$$v_p = \frac{V_{max}\left(s - \frac{p}{K_{eq}}\right)}{s\left(1 + \frac{p}{K_{ii}}\right) + K_{ma}\left(1 + \frac{p}{K_{is}}\right)} \quad (52)$$

where $$V_{max} = \frac{\kappa^2 \alpha m \omega}{\omega + m} \quad (53)$$

$$K_{eq} = \frac{\omega \mu m}{\rho \lambda K (1 - m)} \quad (54)$$

$$K_{ii} = \frac{\omega + m}{\lambda(\rho + \omega)} \quad (55)$$

$$K_{ma} = \frac{m + K(1 - m)}{\mu(\omega + m)} \quad (56)$$

and $$K_{is} = \frac{m + K(1 - m)}{\lambda K(1 - m) + \lambda \rho} \quad (57)$$

$K_{ii}$ and $K_{is}$ are the inhibition constants which represent the effects of [P]$_\infty$ on the slope and the intercept of the 1/v-axis, respectively of the 1/v versus 1/s plot. The values can be calculated from the values of $K_m$ and $V_{max}$; however, a more accurate determination can be made if a series of reciprocal plots are constructed for a wide range of product concentrations. The slope and the 1/I-axis intercept of each can be replotted versus the corresponding product concentration. $K_{iip}$ and $K_{mp}$ can be determined from the replots of the 1/I-axis intercept and slope vs $\lambda$, respectively [Eqs. (58) and (59), respectively].

$$\frac{1}{V_{max,app}} = \frac{1}{V_{mad}K_{iip}}[P] + \frac{1}{V_{max}} \quad (58)$$

$$slope_{1/[S]} = \frac{K_{ma}}{V_{max}K_{mp}}[P] + \frac{K_{ma}}{V_{max}} \quad (59)$$

Where $V_{max,app}$ and $V_{max}$ are the y-intercept at a given λ and the y-intercept when λ=0, respectively.

The observable Thiele modulus ($\Phi_i$), which is the ratio of intrinsic chemical reaction rate in the absence mass transfer limitations to the rate of diffusion through the film, can be estimated using Eq. (60):

$$\Phi_i = \frac{v_i l^2}{D_i K_i C_i} \quad (60)$$

where $D_i$ is the diffusion coefficient of component i into the film and $C_i$ the concentration of species i at the liquid-film interface.

In catalytic reactors, the effectiveness factor (η) is defined as the measured reaction rate divided by the motion rate that would have resulted if there were no diffusional resistance within the film. This latter is obtained by evaluating the reaction rate assuming the concentration throughout the film is equal to that at the film/bulk boundary (χ=1):

$$\eta = \frac{\int_{\chi=0}^{\chi=1} v_P \, d\chi}{\int_{\chi=0}^{\chi=1} v_P\big|_{\chi=1} d\chi} \quad (61)$$

When η is close to 1, the reaction is relatively uninfluenced by diffusion. However, when η is much less than 1, the observed reaction rate is controlled by diffusion within the film.

This mathematical model can be compared to the one previously developed by Bartlett and Pratt (Bartlett and Pratt, 1995) by assuming irreversible enzyme kinetics and irreversible mediator kinetics ($k_B$=0). Under these conditions, Eqs. (41) and (42) reduce to Eqs. (62) and (63), respectively:

$$\frac{\partial^2 m}{\partial \chi^2} = \frac{sm\kappa_*^2}{m\gamma_*(s\mu+1)+s} \text{ and} \quad (62)$$

$$\frac{\partial^2 s}{\partial \chi^2} = \frac{sm\kappa_*^2 \eta_*^{-1} \gamma_*}{m\gamma_*(s\mu+1)+s} \text{ where} \quad (63)$$

$$\kappa_*^2 = \frac{k_A[E_T]l^2}{D_A} \quad (64)$$

$$\eta_* = \frac{D_S k_a(k_{-2}+k_3)}{D_A k_3 k_2} \text{ and} \quad (65)$$

$$\gamma_* = \frac{[M_T]k_a(k_{-2}+k_3)}{k_2 k_3 K_S [S]_\infty} \quad (66)$$

Eq. (66) matches the comparable equation developed by Bartlett and Pratt (Bartlett and Pratt, 1995), suggesting that the irreversible model is a special case of the more general, reversible model developed here.

Figure 11A:
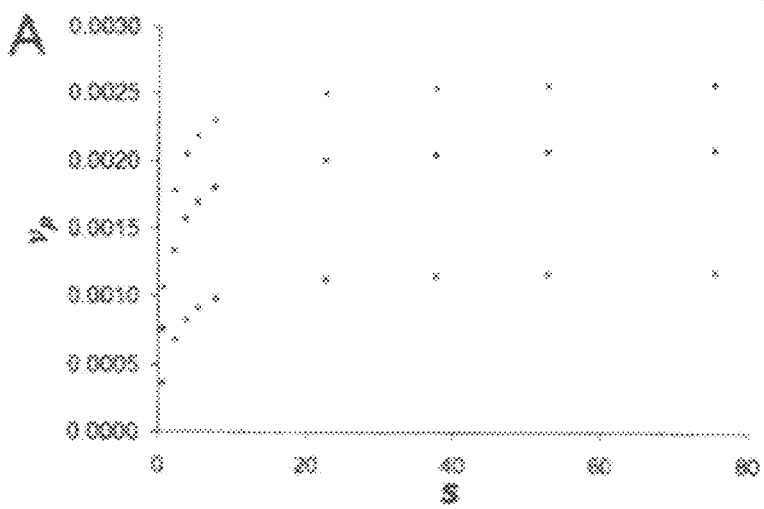
FIGS. 11A and 11B are plots of product formation reaction rate versus dimensionless substrate concentration and the multiplicative reciprocal of product reaction rate versus the multiplicative reciprocal of the dimensionless substrate concentration at various product concentrations.
Figure 11B:
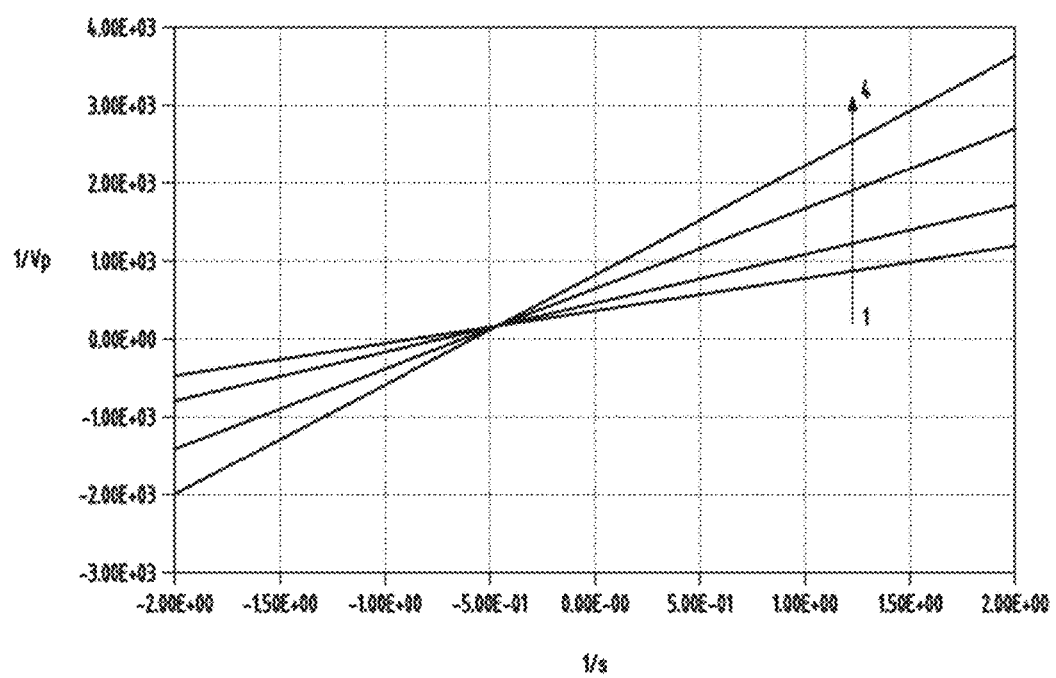

The initial reaction rate dependence on product concentration was derived using the presented mathematical model (FIG. 11A). For reversible enzymes, the product inhibits the enzyme's activity towards the substrate in a manner that resembles enzyme inhibition. To determine the type of inhibition and values of the kinetic constants, the data were plotted in Lineweaver-Burk form (FIG. 11B). FIG. 11B shows the double-reciprocal plot for multiple dimensionless product concentrations. As λ increases, the slope and 1/I-intercepts of the double reciprocal plots increase, pivoting clockwise about a point of intersection that does not lie on either axis. This trend is characterized by a mixed inhibition mechanism. The inhibition constants (Table 2) were estimated from the data presented in FIGS. 11A and 11B.

There are three major regions of the polarization curve of interest: (1) the oxidation current, (2) reduction current, and (3) the transition between the oxidation and the reduction current. These regions of the polarization curve are affected by K, μ, λ, κ, ω, η, α, and β.

Figure 12A:
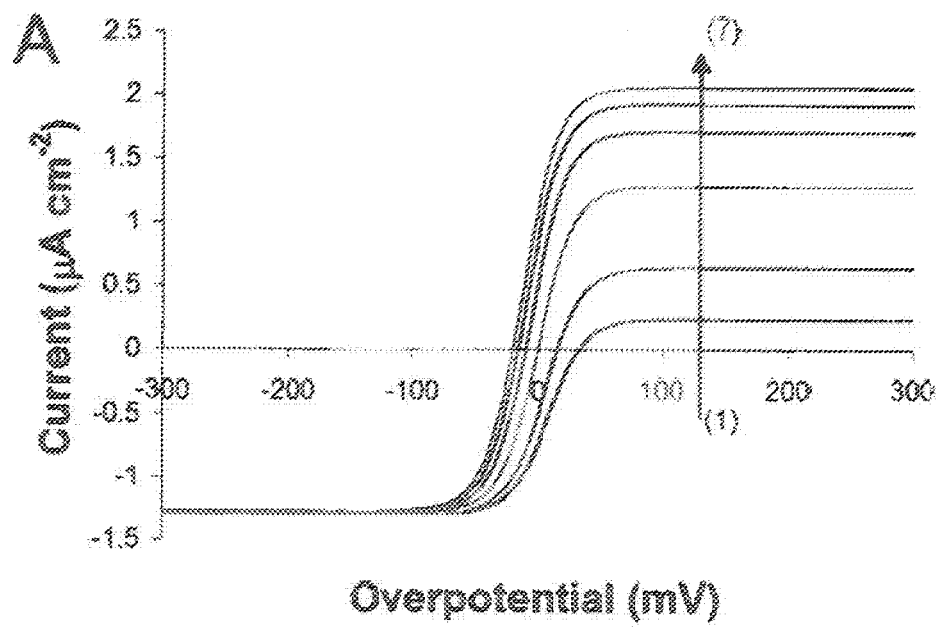
FIGS. 12A and 12B illustrate the effects of the ratios of the substrate and product species concentrations to the Michaelis-Menten constant for the substrate and product, respectively.
Figure 12B:
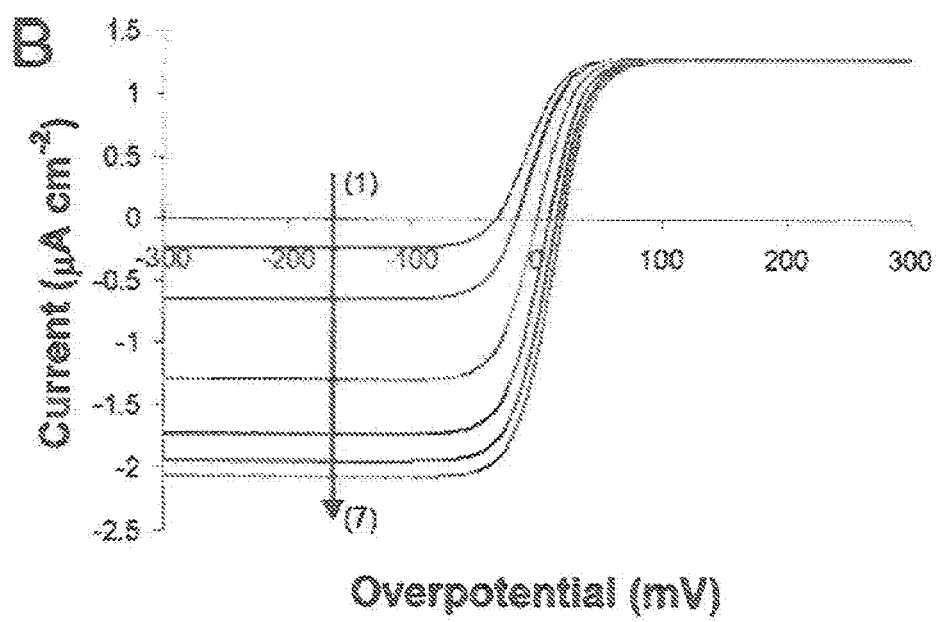

FIGS. 12A and 12B show the effects of substrate concentration (through μ) and product concentration (through λ) on the oxidation current, reduction current, and the apparent oxidation potential of the enzyme/mediator-modified electrode when X=1, Y=1, K=1, λ=1.0, κ=4.6081, ω=0.0015, ρ=0.0015, α–1, and β=1. For μ values less than 0.1, the oxidation current increases proportionally to μ, suggesting that the oxidation current is limited by substrate. As μ exceeds 0.1, the oxidation current begins to saturate, reaching a plateau as μ approaches 3. On the other hand, increasing μ decreases the reduction current, consistent with the idea that μ inhibits the reverse (reduction) reaction. The half-wave potential shifts to more negative potentials (FIG. 12A with increasing μ.

FIG. 12B shows the effect of product concentration (through λ) on the polarization curves. For λ values less than 0.1, the reduction current increases proportionally to λ, suggesting that the reduction current is limited by product. As λ exceeds 0.1, the reduction current begins to saturate, reaching a plateau as λ approaches 3. The increase in the reduction current is accompanied with a decrease in the oxidation current. The half-wave potential shifted to more positive potentials with increasing λ [FIG. 3B].

To further explore the effects of μ and λ on the polarization curves, multiple reaction conditions [X=1, Y=1, K=1.714, κ=2.0608, ω=0.0162, ρ=0.0032, α=0.5714, and β=0.2857) and (X=1, Y=1, K=6.7742, κ=6.6246, ω=0.0029, ρ=0.0088, α=3.0, and β=4.0)] were also examined. For all of these parameter sets, similar trends were observed. Oxidation current increased proportionally with μ for μ values less than 0.1 and then saturated as μ values approached 3. Reduction current increased proportionally with λ for λ values less than 0.1 and then saturated as λ values approached 3. These results suggest that μ and λ strongly influence the system's performance over a wide range of parameter space.

Figure 13A:
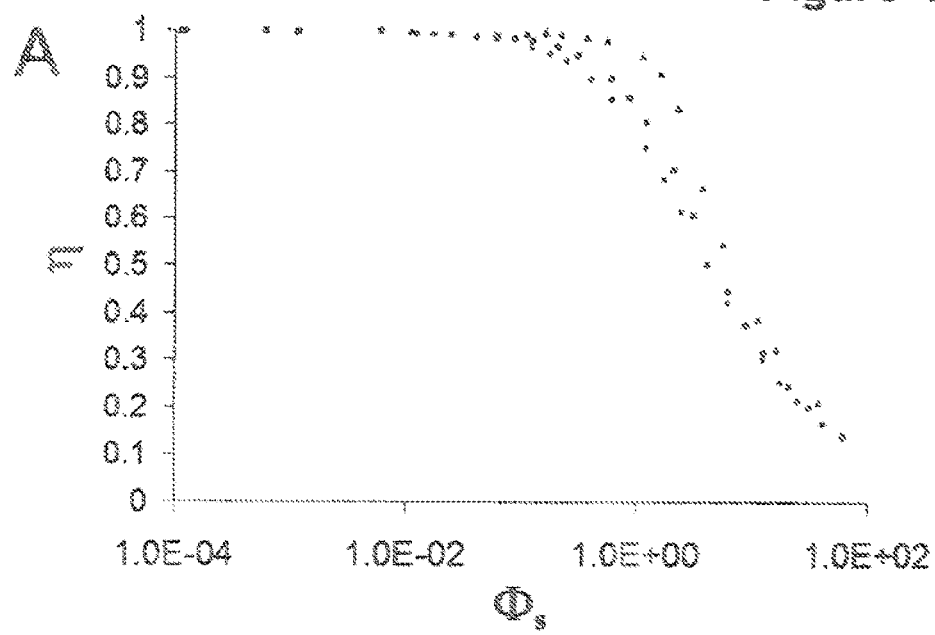
FIGS. 13A and 13B are plots of the effectiveness factor of the bioelectronic interface as a function of the observed Thiele modulus with respect to the substrate and product, respectively.

FIG. 13A shows the plot of η vs. $\Phi_S$ when X=1, Y=1, K=1, λ=1.0, κ=4.6081, ω=0.0015, ρ=0.0015 with varying values of μ. When $\Phi_S$<0.1 η approaches unity, suggesting the bioelectronic interface is kinetically limited. Upon increasing $\Phi_S$>1, η decreases rapidly suggesting that the system becomes substrate diffusion limited. To fully understand the effects of substrate diffusion, multiple reaction conditions [(X=1, Y=1, K=1.714, κ=2.0608, ω=0.0162, and ρ=0.0032) and (X=1, Y=1, K=6.7742, κ=6.6246, ω=0.0029, and ρ=0.0088] were studied (data not shown). For low values of $\Phi_S$ ($\Phi_S$<0.1) η approaches unity; however, when $\Phi_S$ increases ($\Phi_S$>1) η decreases rapidly. Similarities between η vs. $\Phi_S$ plots for the different reaction systems suggest that a single curve can represent the behavior of the bioelectronic interface at highly oxidizing potentials for a range of concentrations and reaction conditions suitable of biocatalytic experiments.

Figure 13B:
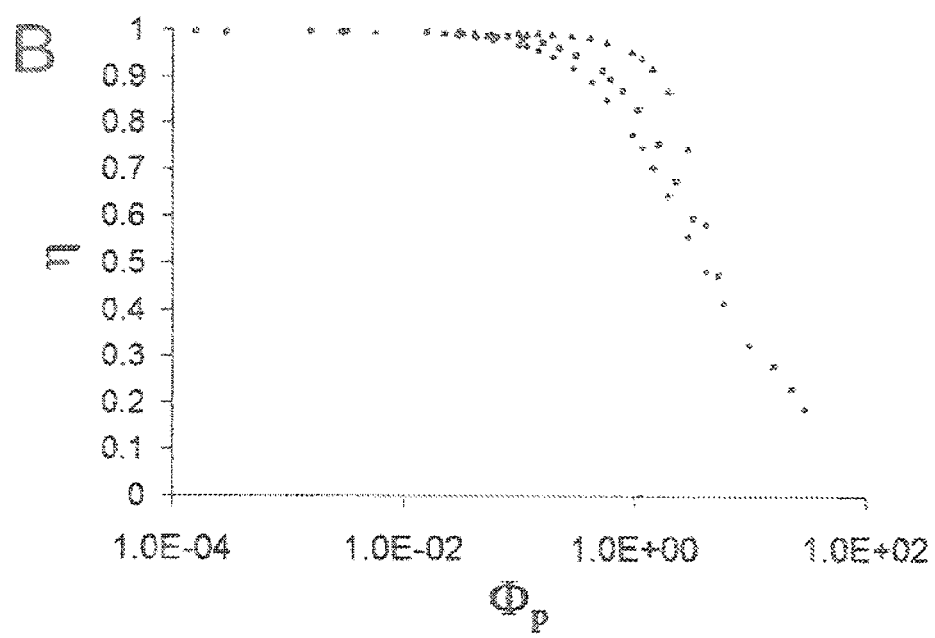

FIG. 13B shows the effect of multiple values of λ on the plot η vs. $\Phi_P$ at various reaction conditions at an applied potential of −250 mV when X=1, Y=1, K=1, μ=1.0, $\kappa=4.6081$, $\omega=0.0015$, and $\rho=0.0015$ at various values of $\lambda$. The bioelectronic interface transitions from a kinetic limited regime to a diffusion limited regime as $\Phi_P$ approaches 0.1. Plots of $\eta$ vs. $\Phi_P$ for multiple $\lambda$ under multiple reaction conditions [(X=1, Y=1, K=1.714, $\kappa=2.0608$, $\omega=0.0162$, and $\rho=0.0032$) and (X=1, Y=1, K=6.7742, $\kappa=6.6246$, $\omega=0.0029$, and $\rho=0.0088$)] (data not shown), transition from the kinetic limited regime when $\Phi_P=0.1$. The plots of $\eta$ vs. $\Phi_P$ suggest that a single curve can represent the behavior of the bioelectronic interface for a range of concentrations and reaction conditions suitable of biocatalytic experiments.

Figure 14:
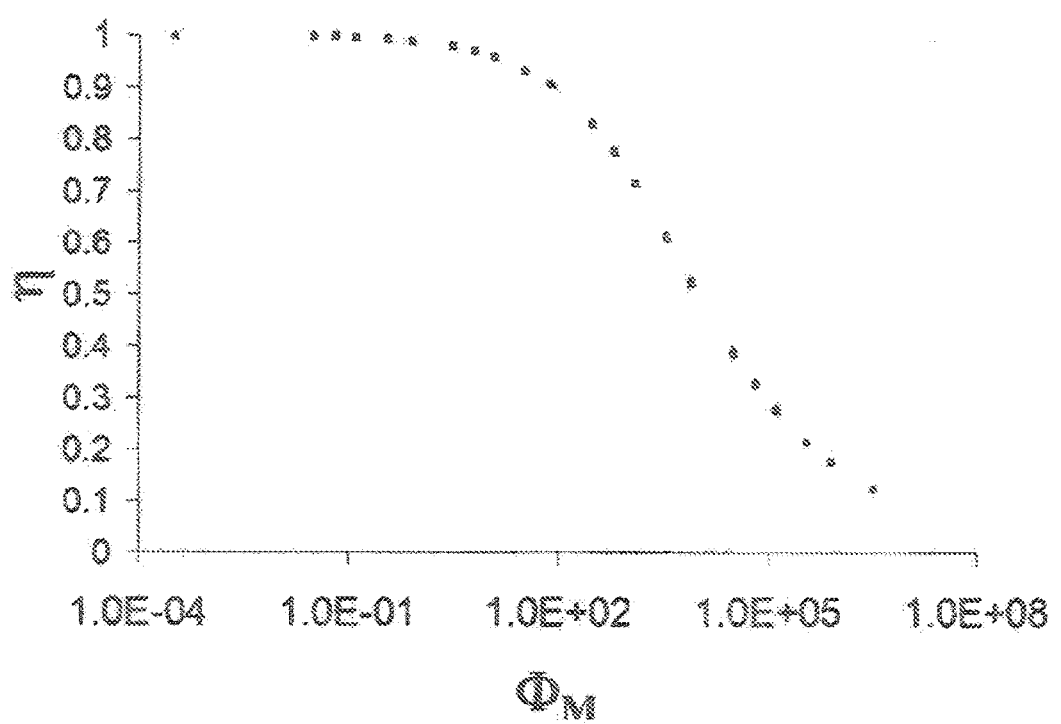
FIG. 14 is a plot of the effectiveness factor of the bioelectronic interface as a function of the observed Thiele modulus for the mediator.

FIG. 14 shows the effects of $D_M$ on the plot of $\eta$ vs. $\Phi_M$ at an applied potential of 250 mV when X=1, Y=1, K–1, $\mu=1.0$, $\lambda=1.0$, $\omega=0.0015$, and $\rho=0.0015$ at various values of m (FIG. 14). For $\Phi_M<0.1$ $\eta$ approaches unity suggesting that the bioelectronic interface is kinetically limited; however, for $\Phi_M>1$ $\eta$ decreases rapidly suggesting that the system transitions form a kinetic limited regime to a diffusion limited regime. The similarity between the plots of $\eta$ vs. $\Phi_M$ suggests that the bioelectronic interface transitions from the kinetic limited to the diffusion limited regime are independent of m. Other reaction conditions [(X=1, Y–1, K=1.714, $\mu=1.0$, $\kappa=2.0608$, $\omega=0.0162$, and $\rho=0.0032$) and (X=1, Y=1, K=6.7742, $\kappa=6.6246$, $\omega=0.0029$, and $\rho=0.0088$)] were examined. When $\Phi_M>0.1$ $\eta$ approaches unity; however, $\eta$ decreases rapidly when $\Phi_M$ is increased. The plots of $\eta$ vs. $\Phi_M$ are consistent with the interface when X=1, Y=1, K=1, $\mu=1.0$, $\lambda=1.0$, $\omega=0.0015$, and $\rho=0.0015$ suggesting a single curve can represent the behavior of the bioelectronic interface for a range of concentrations suitable of biocatalytic experiments.

Figure 15A:
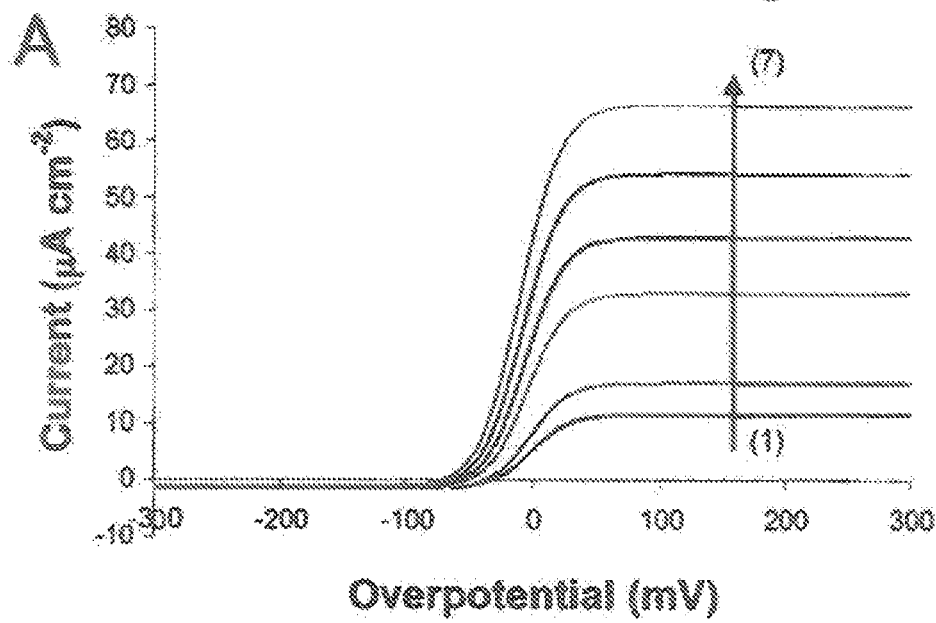
FIGS. 15A and 15B are dimensionless steady state voltammograms at various forward and reverse enzyme reaction rates, respectively.
Figure 15B:
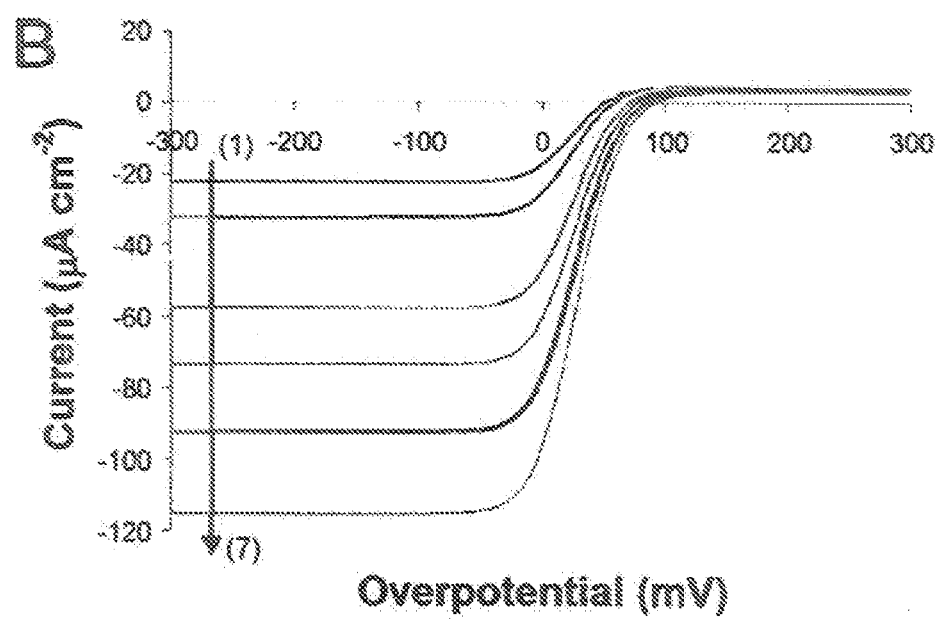

FIGS. 15A and 15B show the effects of $\omega$ and $\rho$ on the polarization curve. For the system where X=1, Y=1, K=1, $\mu=1$, $\lambda=1.0$, $\kappa=4.6081$, $\rho=0.0015$, $\alpha=1$, and $\beta=1$ the oxidation current increased proportionately to of $\omega$ ($\omega \leq 0.015$) [FIG. 6A], suggesting that $\omega$ limits the oxidation current. Increasing $\omega$ ($\omega \geq 0.015$), the increase in current is no longer proportional to $\omega$, suggesting that $\omega$ no longer limits the oxidation current; however, the reduction current decreases suggesting that the reduction current is limited by high values of $\omega$. Upon increasing $\omega$ the half-wave potential becomes more negative.

FIG. 15B shows the effects of polarization curves (X=1, Y=1, K=1, $\mu=1$, $\lambda=1.0$, $\kappa=4.6081$, $\omega=0.0015$, $\alpha=1$, and $\beta=1$) of different values of $\rho$. The reduction current increases proportionately with $\rho$ ($\rho \leq 0.015$); however, increasing $\rho$ ($\rho>0.015$) the current increase is no longer proportional to $\rho$, suggesting that the reduction current is no longer limited by $\rho$. Continuing to increase $\rho$ ($\rho>0.015$) the oxidation current starts to decrease, decreasing the half-wave potential. The effects on the oxidation current, reduction current, and the half-wave potential suggest that $\rho$ and $\omega$ have equal but opposite effects on the bioelectronic interface.

To understand the effects of $\omega$ and $\rho$ on the polarization curves multiple reaction conditions [(X=1.0, Y=1.0, K=1.7143, $\mu=1.0$ $\lambda=1.0$, $\kappa=2.0608$, $\alpha=0.5714$, and $\beta=0.2857$) and (X=1, Y=1.0, K=6.7742, $\mu=1$, $\lambda=1.0$, $\kappa=6.6246$, $\alpha=3.0$, and $\beta=4.0$)] were also examined. For the system where X=1.0, Y=1.0, K=1.7143, $\mu=1.0$, $\lambda=1.0$, $\kappa=1.0608$, $\alpha=0.5714$, and $\beta=0.2857$ the oxidation and reduction current increased proportionately to of $\omega$ and $\rho$ ($\omega \leq 0.015$ and $\rho \leq 0.0015$), when increasing $\omega$ and $\rho$ ($\omega \geq 0.015$ and $\rho \geq 0.015$), the increase in current is no longer proportional to $\omega$ and $\rho$. The half-wave potential for the interface remains constant. For the system where X=1, Y=1.0, K=6.7742, $\mu=1$, $\lambda=1.0$, $\kappa=6.6246$, $\alpha=3.0$, and $\beta=4.0$ the oxidation and reduction current increased proportionately to of $\omega$ and $\rho$ ($\omega \leq 0.015$ and $\rho \leq 0.0015$), when increasing $\omega$ and $\rho$ ($\omega \geq 0.015$ and $\rho \geq 0.015$), the increase in current is no longer proportional to $\omega$ and $\rho$. The half-wave potential for the interface remains constant. The oxidation current, reduction current, and half-wave potential suggests that the effects of $\omega$ and $\rho$ are consistent independent of the reaction conditions.

Figure 16:
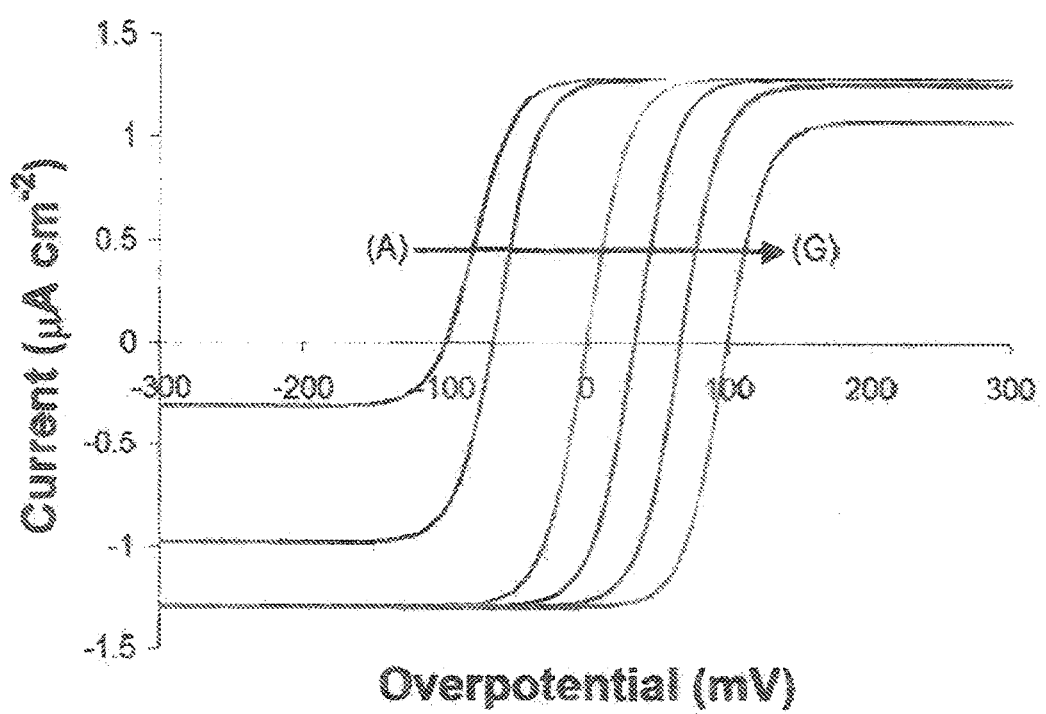
FIG. 16 shows dimensionless steady state voltammograms that illustrate the effect of mediator kinetics on oxidation current, reduction current, and the apparent oxidation over potential of the enzyme/mediator-modified electrode.

FIG. 16, shows the effect of mediator kinetics (K) on the oxidation current, reduction current and the apparent oxidation potential of the enzyme/mediator-modified electrode. The oxidation and reduction current remain stable when changing K between 0.1 and 100. The oxidation and reduction currents began to decrease upon increasing K above 100 or decreasing below 0.1, respectively, suggesting that the mediator kinetics become limiting in these regimes.

The half-wave potential was found to be a function of K, and is given by Eq. (67):

$$\Delta E = \left(\frac{RT}{nF}\right)\ln(K) \qquad (67)$$

where $\Delta E$ is the $E_{1/2}$. Eq. (67) is no longer valid when K becomes limiting.

A unified model for a bioelectronic interface in which an electron mediator and reversible enzyme are entrapped in a uniform film at the electrode surface has been presented. The model can predict performance of the bioelectronic interface for a given set of parameters (enzyme kinetics, mediator kinetics, substrate/product diffusion, mediator diffusion, substrate/product concentration, mediator concentration and electrode potential), which can be determined experimentally. This predictive capability provides a mechanism to rationally design and optimize bioelectronic interfaces for applications in biosensors, biocatalytic reactors, and biological fuel cells.

The above description is considered that of the preferred embodiments only. Modifications of the invention will occur to those skilled in the art and to those who make or use the invention. Therefore, it is understood that the embodiments shown in the drawings and described above are merely for illustrative purposes and not intended to limit the scope of the invention, which is defined by the following claims as interpreted according to the principles of patent law, including the doctrine of equivalent.

The invention claimed is:

1. A bioelectronic device comprising:
   an electrically conductive carbon electrode; and
   a bioelectronic interface bonded to a surface of the electrically conductive carbon electrode, and configured to regenerate, the bioelectronic interface including a catalytically active material that facilitates electron transfer, the catalytically active material configured to be releasably and electrostatically bound directly or indirectly to the surface via a polyelectrolyte, wherein the polyelectrolyte is configured to be removably and electrostatically bound to a non-thiol ionic linker that is covalently bound to a carbon atom at the surface.

2. The device of claim 1, wherein the catalytically active material includes an enzyme that is bound directly or indirectly to the polyelectroly.

3. The device of claim 2, wherein the enzyme is an oxidoreductase, a dehydrogenase, a secondary alcohol dehydrogenase or a mannitol dehydrogenase.

4. The device of claim 1, wherein the non-thiol ionic linker is glycine.

5. The device of claim 1, wherein said polyelectrolyte is comprised of a compound that includes a linking moiety covalently bound to the carbon atom at the surface of the electrically conductive carbon electrode, and further includes at least one ionized moiety for achieving the direct or indirect electrostatic bonding of the catalytically active material to the electrically conductive carbon electrode.

6. The device of claim 1 wherein the electrically conductive carbon electrode further includes a carbon substrate.

7. The device of claim 6, wherein the carbon substrate is a vitreous carbon substrate.

8. The device of claim 7, wherein the vitreous carbon substrate is a reticulated vitreous carbon electrode.

9. The device of claim 1, wherein the bioelectronic interface further comprises a redox cofactor that facilitates or enhances activity of the catalytically active material.

10. The device of claim 9, wherein the bioelectronic interface includes an electron mediator that reduces the electrical potential needed to transfer electrons during a chemical reaction.

11. The device of claim 10, wherein the electron mediator is toluidine blue O, neutral red or Nile blue A.

12. The device of claim 9, wherein the redox cofactor is covalently bound to a polyelectrolyte that is electrostatically bound directly or indirectly to the surface of the electrically conductive carbon electrode.

13. The device of claim 9, wherein the redox cofactor is selected from nicotinamide adenine dinucleotide (NAD), nicotinamide adenine dinucleotide phosphate (NADP), flavin adenine dinucleotide (FAD), flavin mononucleotide (FMN), and combinations thereof.

14. The device of claim 12, wherein a boronate linkage is used to bind the redox cofactor to said polyelectrolyte.

15. The device of claim 1, wherein the polyelectrolyte is polyethyleneimine.

16. The device of claim 1, wherein the catalytically active material is associated with polyelectrolyte multilayers (PEMs) that are bound together by alternating layers of oppositely charged polyelectrolytes.

17. The device of claim 16, wherein a redox cofactor is associated with PEMs that are bound together by alternating layers of oppositely charged polyelectrolytes.

18. The device of claim 16, wherein a redox cofactor and an electron mediator are associated with PEMs that are bound together by alternating layers of oppositely charged polyelectrolytes.

19. The device of claim 16, wherein the oppositely charged polyelectrolytes are polyethyleneimine (PEI) and polyacrylic acid (PAA).

20. The device of claim 1, wherein the polyelectrolyte ionically bonds a dehydrogenase enzyme and a redox cofactor to an ionically functionalized, electrically conductive carbon electrode to which an electron mediator is bound.

21. The device of claim 20, wherein the catalytically active material includes at least two different catalytically active components.

22. The device of claim 21, wherein said catalytically active components comprise different enzymes that catalyze different reactions.

23. The device of claim 22 wherein said enzymes comprise a xylose isomerase and a mannitol dehydrogenase.

24. The device of claim 22, wherein a branched linking moiety and the polyelectrolyte are used to couple the enzymes, and optionally couple a redox cofactor for one or both of the enzymes, and/or optionally couple an electron mediator for one or both of the redox cofactors.

25. The device of claim 1, wherein the covalent bond with a carbon atom is a carbon-nitrogen bond.

26. The device of claim 1 containing no thiol linkages.

27. The device of claim 1 wherein said interface is molecularly self-assembled.

28. The device of claim 2, wherein the polyelectrolyte provides enzymatic surface coverage up to about $3.3 \times 10^{-11}$ moles/cm$^2$.

29. The device of claim 16 wherein each of the PEMs has a thickness between about one and about five nanometers.

30. A method comprising:
producing a bioelectronic device comprising bonding a bioelectronic interface to a surface of an electrically conductive carbon electrode, wherein the bioelectronics interface is configured to regenerate, the bioelectronic interface including a catalytically active material that facilitates electron transfer, the catalytically active material configured to be releasably and electrostatically bound directly or indirectly to the surface via a polyelectrolyte, wherein the polyelectrolyte is configured to be removably and electrostatically bound to a non-thiol ionic linker that is covalently bound to a carbon atom at the surface.

* * * * *

UNITED STATES PATENT AND TRADEMARK OFFICE
CERTIFICATE OF CORRECTION

PATENT NO. : 10,246,786 B2  
APPLICATION NO. : 15/177668  
DATED : April 2, 2019  
INVENTOR(S) : Robert Mark Worden et al.

Page 1 of 1

It is certified that error appears in the above-identified patent and that said Letters Patent is hereby corrected as shown below:

On the Title Page  
Other Publications/Page 3/Column 2/Pogorelova/Line 12: Error reads as "with on-Sensitive" and should read as "with Ion-Sensitive"

In the Specification  
Column 3/Line 38: Error reads as "optimum, thickness" and should read as "optimum thickness"  
Column 3/Line 60: Error reads as "Fe(CN)6$^{-3}$" and should read as "Fe(CN)$_6^{-3}$"  
Column 3/Line 61: Error reads as "Fe(CN)6$^{-4}$" and should read as "Fe(CN)$_6^{-4}$"  
Column 5/Line 33: Error reads as "an inorganic" and should read as "an organic"  
Column 16/Line 65: Error reads as "4.4 mg mL$^{-1}$" and should read as "4.4 mg/mL$^{-1}$"  
Column 17/Line 2: Error reads as "fro either" and should read as "from either"  
Column 19/Line 3: Error reads as "Fe(CN$_6^{-4}$" and should read as "Fe(CN)$_6^{-4}$"  
Column 19/Line 19: Error reads as "1991); non-uniform" and should read as "1991); and non-uniform"  
Column 22/Line 5: Error reads as "electron hoping" and should read as "electron hopping"  
Column 22/Line 10: Error reads as "electron hoping" and should read as "electron hopping"  
Column 23/Lines 2-3: Error reads as "modified electrode-modified electrode" and should read as "modified electrode"  
Column 24/Line 35: Error reads as "a 0.22☐m" and should read as "a 0.22 µm"  
Column 27/Line 24: Error reads as "cases is which" and should read as "cases in which"  
Column 27/Line 31: Error reads as "1994." and should read as "1994)."  
Column 27/Line 38: Error reads as "develop a" and should read as "developed a"  
Column 27/Line 51: Error reads as "analysts presented" and should read as "analysis presented"  
Column 35/Line 35: Error reads as "to of" and should read as "to"  
Column 35/Line 54: Error reads as "ωand ρ" and should read as "ω and ρ"

In the Claims  
Column 36/Claim 2/Line 62: Error reads as "polyelectroly." and should read as "polyelectrolyte."

Signed and Sealed this  
Fourth Day of June, 2019

Andrei Iancu  
*Director of the United States Patent and Trademark Office*